US009415179B2

(12) United States Patent
Molnar

(10) Patent No.: US 9,415,179 B2
(45) Date of Patent: Aug. 16, 2016

(54) MEDICAL DEVICE, AND THE METHODS OF USING SAME

(71) Applicant: WM & DG, Inc., Deerfield, IL (US)

(72) Inventor: Robert Molnar, Long Grove, IL (US)

(73) Assignee: WM & DG, INC., Deerfield, IL (US)

( * ) Notice: Subject to any disclaimer, the term of this patent is extended or adjusted under 35 U.S.C. 154(b) by 465 days.

(21) Appl. No.: 13/947,610

(22) Filed: Jul. 22, 2013

(65) Prior Publication Data
US 2014/0309494 A1 Oct. 16, 2014

Related U.S. Application Data

(63) Continuation-in-part of application No. 13/486,549, filed on Jun. 1, 2012.

(60) Provisional application No. 61/674,924, filed on Jul. 24, 2012.

(51) Int. Cl.
A61B 1/04 (2006.01)
A61M 16/04 (2006.01)
A61B 7/00 (2006.01)
(Continued)

(52) U.S. Cl.
CPC .......... A61M 16/04 (2013.01); A61B 1/05 (2013.01); A61B 1/0676 (2013.01); A61B 1/0684 (2013.01); A61B 1/267 (2013.01); A61B 7/003 (2013.01); A61M 16/042 (2014.02); A61M 16/0409 (2014.02); A61M 16/0463 (2013.01); A61M 16/0488 (2013.01); A61M 2205/3375 (2013.01); A61M 2205/502 (2013.01); A61M 2230/04 (2013.01)

(58) Field of Classification Search
USPC .......................... 600/114–115, 120–125, 194
See application file for complete search history.

(56) References Cited

U.S. PATENT DOCUMENTS 4,231,365 A 11/1980 Scarberry
4,360,008 A 11/1982 Corazzelli, Jr.
(Continued)

FOREIGN PATENT DOCUMENTS

EP 0 665 029 A2 8/1995
WO 03/084719 A2 10/2003
(Continued)

OTHER PUBLICATIONS http://worldnetdaily.co.uk/markets/news/read/20671060/etview_medical.
(Continued)

Primary Examiner — Matthew J Kasztejna
(74) Attorney, Agent, or Firm — Greer, Burns & Crain, Ltd.

(57) ABSTRACT

A medical device is provided for insertion into a cavity of a patient to visual the internal membranes of the patient. The medical device can be an endotracheal tube, a suction tube, a bronchoscope, a tube changer, an esophageal tube, an intubating tube, an esophageal tube in combination with a separate intubating tube, a device for manipulating the position of the epiglottis of the patient, a stylet, or a tube insertable into the vagina of the patient. The medical device has a camera lumen having a sealed window at one end thereof attached thereto, and a separate camera which is insertable into the camera lumen and is removable from the camera lumen. The camera is used to monitor the internal membranes of the patient during the medical procedure.

7 Claims, 28 Drawing Sheets

(51) Int. Cl.
*A61B 1/05* (2006.01)
*A61B 1/06* (2006.01)
*A61B 1/267* (2006.01)

(56) References Cited

U.S. PATENT DOCUMENTS

| | | | |
|---|---|---|---|
| 4,577,638 A | 3/1986 | Graham | |
| 4,584,998 A | 4/1986 | McGrail | |
| 4,607,643 A | 8/1986 | Bell et al. | |
| 5,052,386 A | 10/1991 | Fischer, Jr. | |
| 5,193,692 A | 3/1993 | Farley et al. | |
| 5,241,956 A | 9/1993 | Brain | |
| 5,353,787 A | 10/1994 | Price | |
| 5,400,771 A * | 3/1995 | Pirak | A61B 1/042 128/200.26 |
| 5,499,625 A | 3/1996 | Frass et al. | |
| 5,511,915 A | 4/1996 | Farley et al. | |
| 5,511,916 A | 4/1996 | Farley et al. | |
| 5,513,627 A | 5/1996 | Flam | |
| 5,632,271 A | 5/1997 | Brain | |
| 5,682,880 A | 11/1997 | Brain | |
| 5,740,791 A | 4/1998 | Aves | |
| 5,819,733 A | 10/1998 | Bertram | |
| 5,888,195 A | 3/1999 | Schneider | |
| 6,142,144 A | 11/2000 | Pacey | |
| 6,189,533 B1 | 2/2001 | Simon et al. | |
| 6,196,225 B1 | 3/2001 | Allgeyer | |
| 6,349,720 B1 | 2/2002 | Clark | |
| 6,386,199 B1 | 5/2002 | Alfery | |
| 6,439,232 B1 | 8/2002 | Brain | |
| 6,440,061 B1 | 8/2002 | Wenner et al. | |
| 6,443,156 B1 | 9/2002 | Niklason et al. | |
| 6,543,447 B2 | 4/2003 | Pacey | |
| 6,626,169 B2 | 9/2003 | Gaitini | |
| 6,631,720 B1 | 10/2003 | Brain | |
| 6,634,354 B2 | 10/2003 | Christopher | |
| 6,655,377 B2 | 12/2003 | Pacey | |
| 6,860,264 B2 | 3/2005 | Christopher | |
| 6,918,391 B1 | 7/2005 | Moore | |
| 7,052,456 B2 | 5/2006 | Simon | |
| 7,128,509 B2 | 10/2006 | Farley et al. | |
| 7,156,091 B2 | 1/2007 | Koyama et al. | |
| 7,237,993 B2 | 7/2007 | Farley et al. | |
| 7,331,925 B2 | 2/2008 | McMorrow et al. | |
| 7,450,746 B2 | 11/2008 | Yang et al. | |
| 7,520,857 B2 | 4/2009 | Chalana et al. | |
| 7,527,601 B2 | 5/2009 | Dubey et al. | |
| 7,611,466 B2 | 11/2009 | Chalana et al. | |
| 7,654,970 B2 | 2/2010 | Dubey | |
| 7,713,216 B2 | 5/2010 | Dubey et al. | |
| 7,727,150 B2 | 6/2010 | Chalana et al. | |
| 7,744,534 B2 | 6/2010 | Chalana et al. | |
| 7,749,165 B2 | 7/2010 | McMorrow et al. | |
| 7,749,176 B2 | 7/2010 | Dubey | |
| 7,811,239 B2 | 10/2010 | Dubey et al. | |
| 7,819,806 B2 | 10/2010 | Yang et al. | |
| 7,854,324 B2 | 12/2010 | Farley et al. | |
| 7,896,007 B2 | 3/2011 | Brain | |
| 7,921,847 B2 * | 4/2011 | Totz | A61M 16/04 128/200.26 |
| 7,976,458 B2 | 7/2011 | Stefanchik et al. | |
| 8,016,760 B2 | 9/2011 | Chalana et al. | |
| 8,038,629 B2 | 10/2011 | Solanki et al. | |
| 8,202,215 B2 | 6/2012 | Xiao et al. | |
| 8,215,307 B2 | 7/2012 | Nasir | |
| 8,297,275 B2 | 10/2012 | Ogilvie et al. | |
| 8,529,442 B2 | 9/2013 | Pacey et al. | |
| 2005/0182297 A1 | 8/2005 | Gravenstein et al. | |
| 2006/0111633 A1 | 5/2006 | McMorrow et al. | |
| 2006/0162730 A1 | 7/2006 | Glassenberg et al. | |
| 2006/0180155 A1 | 8/2006 | Glassenberg et al. | |
| 2006/0276694 A1 | 12/2006 | Gandarias | |
| 2007/0137651 A1 | 6/2007 | Glassenberg et al. | |
| 2007/0156068 A1 | 7/2007 | Dubey | |
| 2007/0180887 A1 | 8/2007 | Frenken | |
| 2007/0203393 A1 | 8/2007 | Stefanchik | |
| 2007/0239197 A1 | 10/2007 | Dubey | |
| 2007/0255185 A1 | 11/2007 | Dubey | |
| 2008/0029100 A1 | 2/2008 | Glassenberg et al. | |
| 2008/0114268 A1 | 5/2008 | Dubey | |
| 2008/0146879 A1 | 6/2008 | Pacey | |
| 2008/0188774 A1 | 8/2008 | Dubey | |
| 2008/0276932 A1 | 11/2008 | Bassoul | |
| 2009/0194114 A1 | 8/2009 | Chen et al. | |
| 2009/0227835 A1 * | 9/2009 | Terliuc | A61B 1/00082 600/106 |
| 2010/0113916 A1 * | 5/2010 | Kumar | A61B 5/06 600/424 |
| 2010/0249639 A1 | 9/2010 | Bhatt | |
| 2010/0261967 A1 | 10/2010 | Pacey et al. | |
| 2011/0030694 A1 | 2/2011 | Schaner et al. | |
| 2011/0178372 A1 | 7/2011 | Pacey et al. | |
| 2011/0201882 A1 | 8/2011 | Schwartz et al. | |
| 2011/0315147 A1 | 12/2011 | Wood et al. | |
| 2012/0259173 A1 | 10/2012 | Waldron et al. | |
| 2012/0260921 A1 | 10/2012 | Sangwan | |
| 2013/0030249 A1 | 1/2013 | Vazales et al. | |
| 2014/0194694 A1 | 7/2014 | Chen | |

FOREIGN PATENT DOCUMENTS

| | | |
|---|---|---|
| WO | WO 2008/123934 A1 | 10/2008 |
| WO | 2009025843 A1 | 2/2009 |
| WO | 2012/080293 A2 | 6/2012 |
| WO | 2013/017535 A2 | 2/2013 |

OTHER PUBLICATIONS http://www.cardiomed.com/products/anesthesiology?task=callelement&format=raw&item_id=113&element=be8726ed-4912-4242-951f-765db1f52b3f&method=download.
http://www.etview.com/index_old.php.
http://www.etview.com/sites/all/themes/etview/docs/ETV_A16703_ETView_Brochure.pdf.
http://finance.yahoo.com/news/etview-medical-ltd-announces-appointment-104300770.html.
http://www.aja-online.com/fileadmin/user_upload/Edition_pdfs/2011/Vol-12_1-2011/03._22-33_Laryngeal_tube_a_review_of_current_literature.pdf.
How to Use a JEM Endotracheal Tube Changer, 2 pages.
Bledsoe, "The Disappearing Endotracheal Tube"., Clinical Professor of Emergency Medicine, University of Nevada School of Medicine.
"Incubation Threatened by New Devices and Lack of Paramedic Practice", Patient Care, Jems.com; http://www.jems.com/article/patient-care/incubation-threatened-new-devi.
"Incubation Threatened by New Devices and Lack of Paramedic Practice", Patient Care; http://www.jems.com/article/patient-care/intubation-threatened-new-devi.
"Continuous Airway Control"; Vivasight.
Genzwuerker, MD. et al. "Laryngeal tube: a review of current literature" AJA-Online.com 2011:vol. 12.
Kidali MD, "Capnography in emergency medicine-911" http://www.capnography.com/outside/922.htm.
VivaSight, Airway management for lung isolation, ETVIEW.
ETView Medical, Ltd., Announces Exclusive Patent License Agreement—Feb. 22, 2012. ETVIEW.
ETVIEW, http://www.etview.com/index_old.php.
VivaSight-SL, ETVIEW.
How to Use a Jem Endotrachael Tube Changer.
ETView Medical, Ltd., Announces Exclusive Patent License Agreement—Feb. 2, 2012, http://worldnetdaily.com.uk/markets/news/read/20671060/etview_medical, Jul. 5, 2012.

* cited by examiner

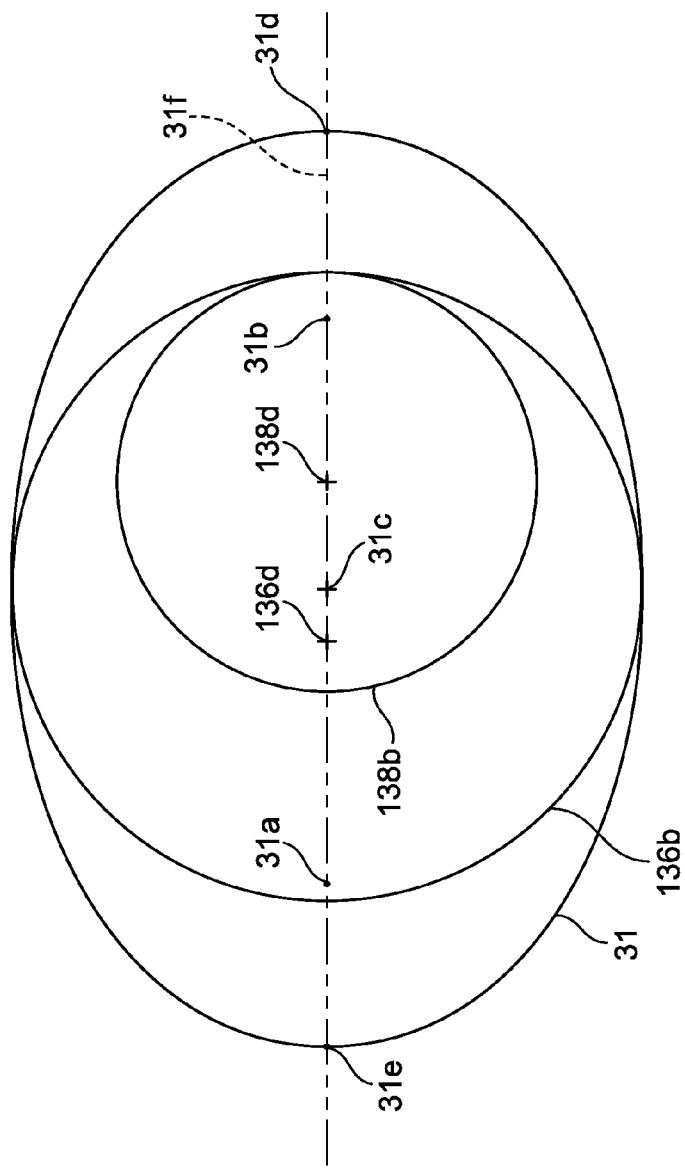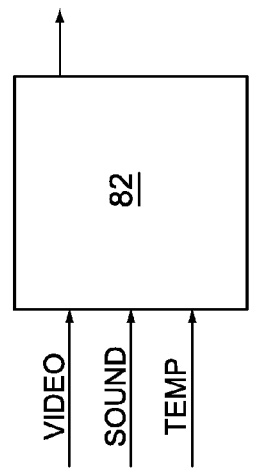

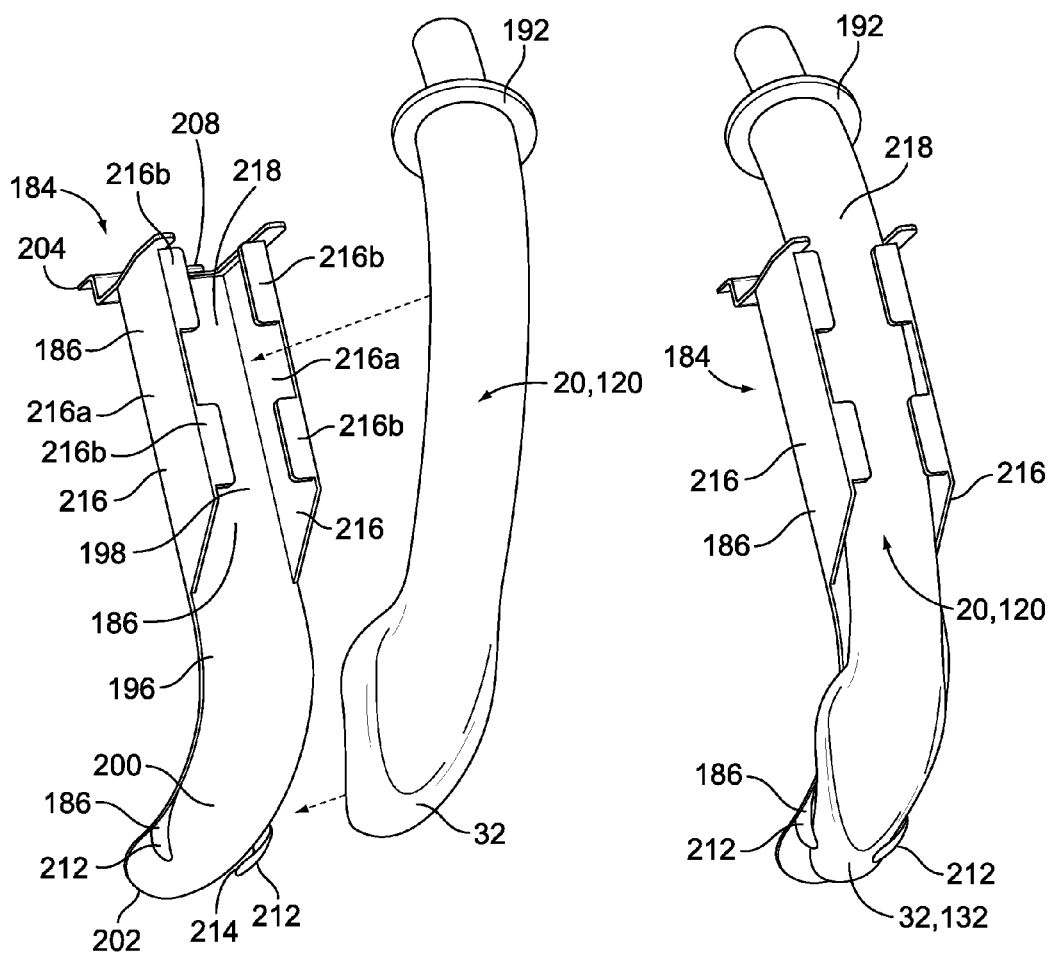
FIG. 17  FIG. 18

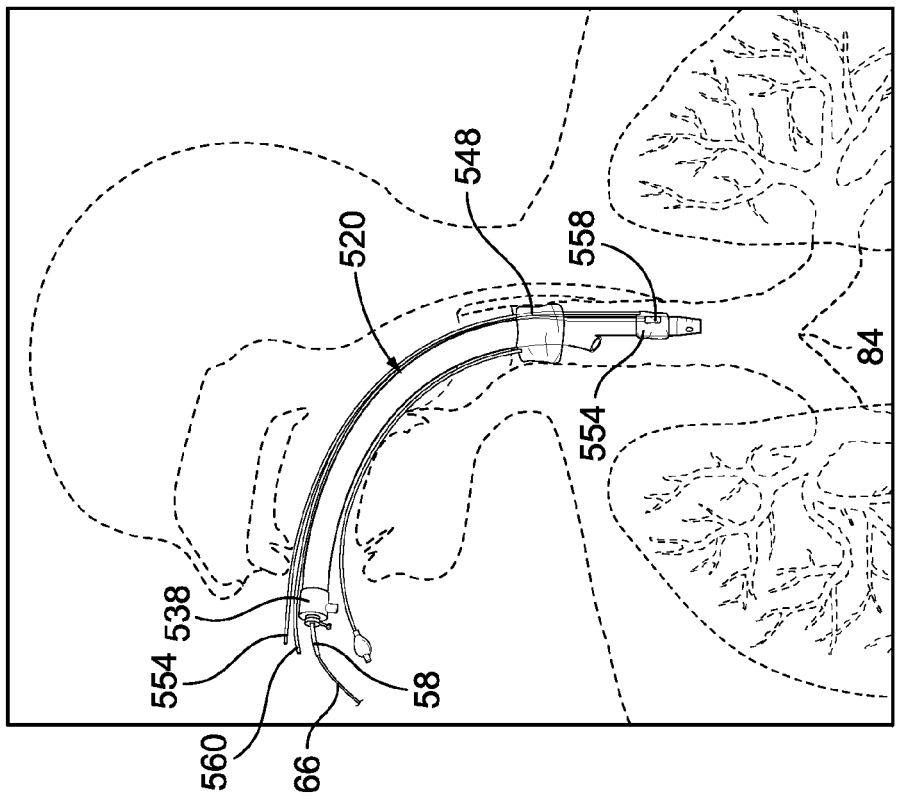
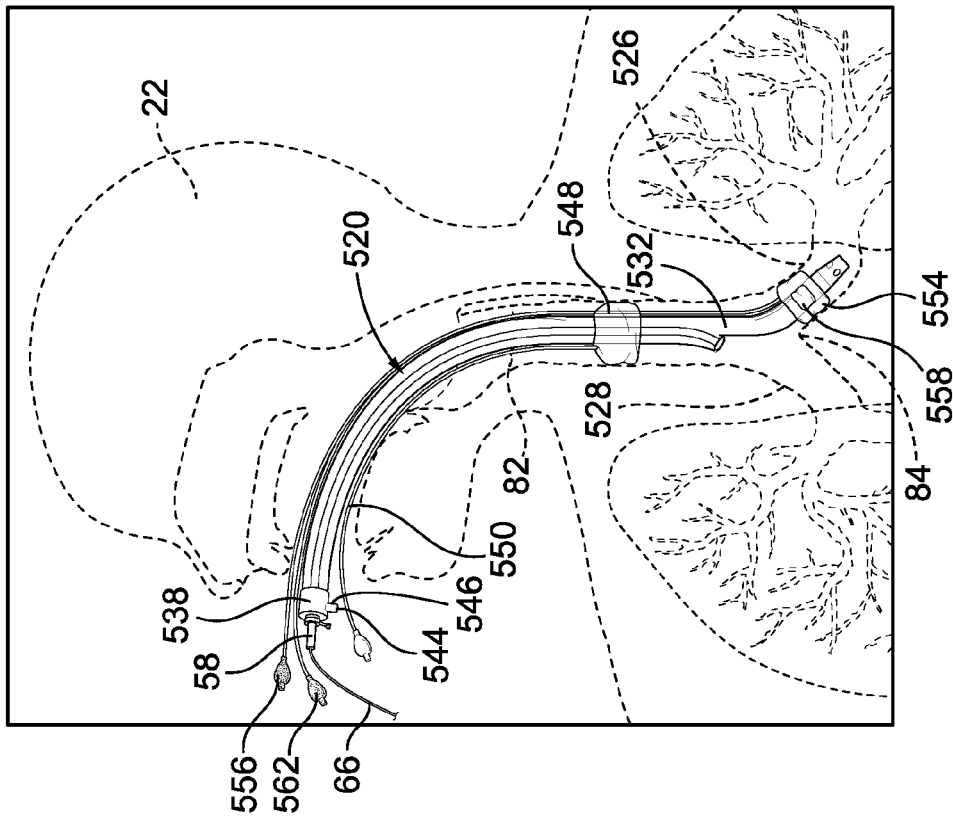

MEDICAL DEVICE, AND THE METHODS OF USING SAME

This application is a continuation-in-part application of U.S. Ser. No. 13/486,549, filed on Jun. 1, 2012, the disclosure of which is incorporated in its entirety. This application claims the domestic benefit of U.S. Ser. No. 61/674,924, filed on Jul. 24, 2012, the disclosure of which is incorporated in its entirety.

FIELD OF THE INVENTION

The present invention relates to a medical device for allowing a medical professional to see the internal membranes of a patient during a medical procedure.

BACKGROUND OF THE INVENTION

An example of a medical device which medical professionals use to see the internal membranes of a patient is a laryngeal mask airway. A laryngeal mask airway is used to ventilate and to supply anesthetic to a patient during surgery. A laryngeal mask airway is different than an endotracheal tube in that the laryngeal mask airway is positioned in the throat of the patient proximally of the vocal folds, while an endotracheal tube is passed through the vocal folds and is positioned in the patient's trachea.

Laryngeal mask airways of the prior art generally have a tube opening into the center of a generally elliptical dome. The tube is generally straight, but can flex to assume a curved shape. A cuff, which may be inflatable, is sometimes attached to the perimeter of the dome.

In use, the medical professional inserts the laryngeal mask airway into the mouth of the patient. The open tube allows the patient to breathe on his/her own during insertion. The tube can also be connected to a ventilator to provide assisted breathing to the patient. For insertion, the cuff (if provided), the dome and the tube slide against the hard palate and then against the soft palate and into the pharynx of the patient. This procedure is performed blindly and only by feel which comes from experience in performing the procedure. Trauma to the patient may occur when placing the laryngeal mask airway as a result of the laryngeal mask airway attempting to conform to a curved position in the pharynx. When properly positioned in the hypo-pharynx, the proximal end of the cuff seats against the epiglottis pushing it toward the tongue of the patient and the distal end of the cuff seats in the esophagus. At times, the cuff may be positioned such that the epiglottis is pushed downwardly and may at least partially block the tube opening. This is not a desirable result as the blocking by the epiglottis can cause problems with the airflow through the laryngeal mask airway. In addition, inappropriate sizing and differences in the anatomy of patients may also impair the proper positioning of the laryngeal mask airway. Since the insertion is performed blindly, the medical professional will not know if proper placement of the laryngeal mask airway has occurred. After positioning the laryngeal mask airway, the inflatable cuff (if provided) is inflated and the patient's esophagus is blocked by the cuff. The medical professional will listen for breath sounds and ascertain end tidal $CO_2$ gases from the patient to verify proper positioning of the laryngeal mask airway.

If the medical professional needs to insert an endotracheal tube into the patient, the endotracheal tube can be inserted through the tube of the laryngeal mask airway to intubate the patient. If the epiglottis is at least partially blocking the opening in the tube, this intubation may be difficult. In addition, the glottis opening quite often does not align with the tube opening which can make this blind insertion difficult and may result in trauma to the laryngeal inlet.

A medical device is provided herein which provides improvements to existing laryngeal mask airways and which overcomes the disadvantages presented by the prior art. Other features and advantages will become apparent upon a reading of the attached specification, in combination with a study of the drawings.

SUMMARY OF THE INVENTION

A medical device is provided for insertion into a cavity of a patient to visual the internal membranes of the patient. The medical device can be an endotracheal tube, a suction tube, a bronchoscope, a tube changer, an esophageal tube, an intubating tube, an esophageal tube in combination with a separate intubating tube, a device for manipulating the position of the epiglottis of the patient, a stylet, or a tube insertable into the vagina of the patient. The medical device has a camera lumen having a sealed window at one end thereof attached thereto, and a separate camera which is insertable into the camera lumen and is removable from the camera lumen. The camera is used to monitor the internal membranes of the patient during the medical procedure.

BRIEF DESCRIPTION OF THE DRAWINGS

The organization and manner of the structure and operation of the invention, together with further objects and advantages thereof, may best be understood by reference to the following description, taken in connection with the accompanying drawings, wherein like reference numerals identify like elements in which:

FIG. 10 is a schematic view of the medical device of FIG. 9;

FIG. 11 is a schematic of a control system for use with the medical devices shown in the drawings;

FIG. 17 is a perspective view of an alternate airway assist device which incorporates the features of the present invention for use with the medical devices of FIGS. 1 and 9/10;

FIG. 18 is a perspective view of the airway assist device of FIG. 17 with a medical device mounted therein;

FIGS. 37A and 37B show the medical device of FIG. 36 in use in a patient;

FIGS. 38-39C show perspective views of a further medical device which incorporates the features of the present invention;

DETAILED DESCRIPTION OF THE ILLUSTRATED EMBODIMENTS

Figure 1:
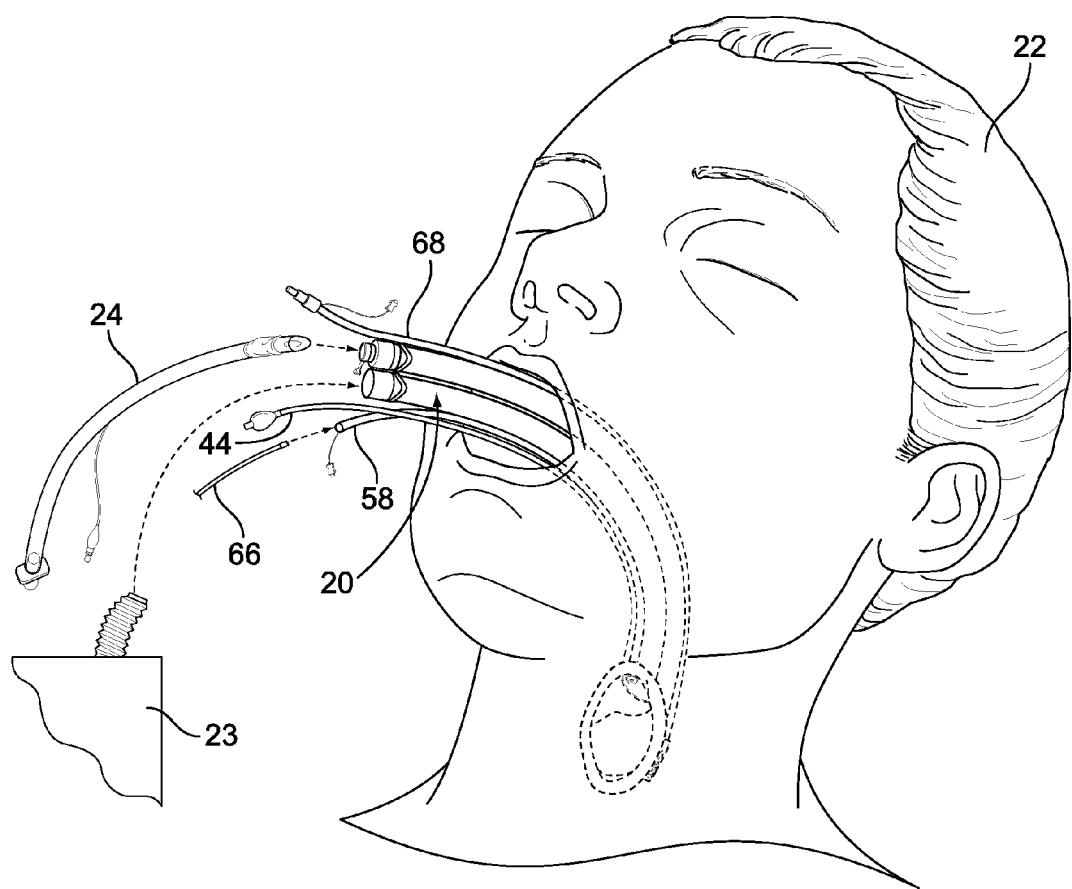
FIG. 1 is a perspective view of a medical device which incorporates the features of the present invention, the medical device being inserted into a patient, and shown with an endotracheal tube and a ventilator which are capable of being used with the medical device.
Figure 2:
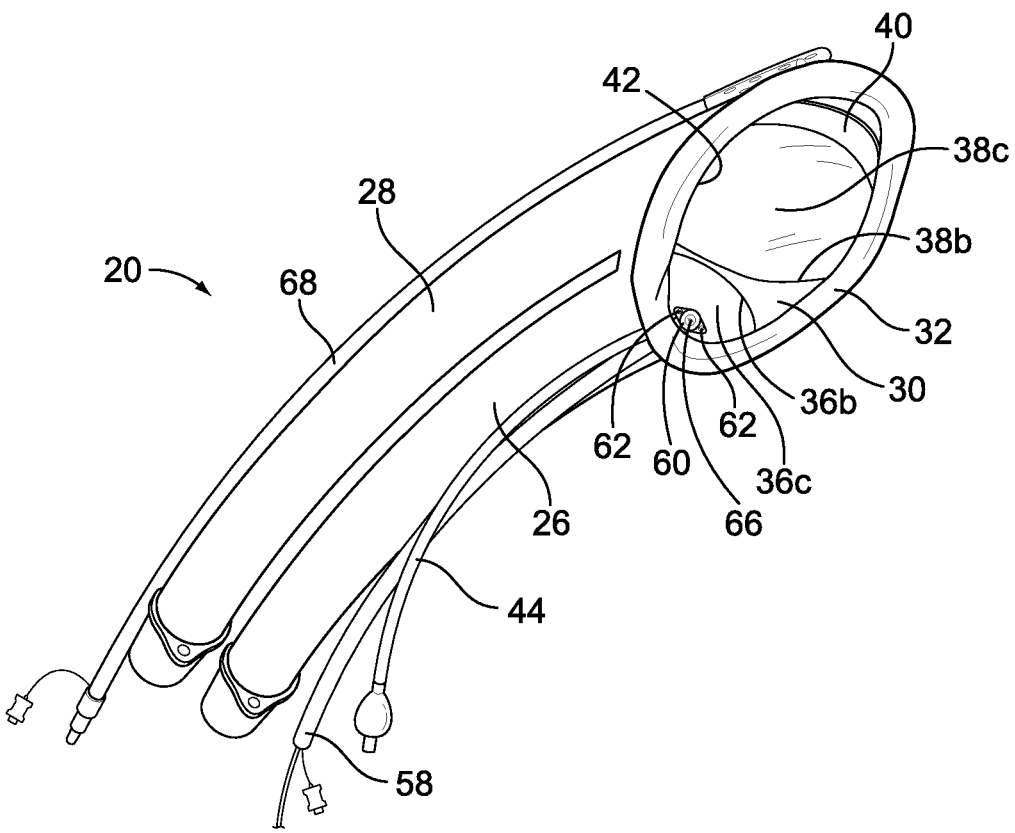
FIG. 2 is a perspective view of the medical device of FIG. 1.
Figure 3:
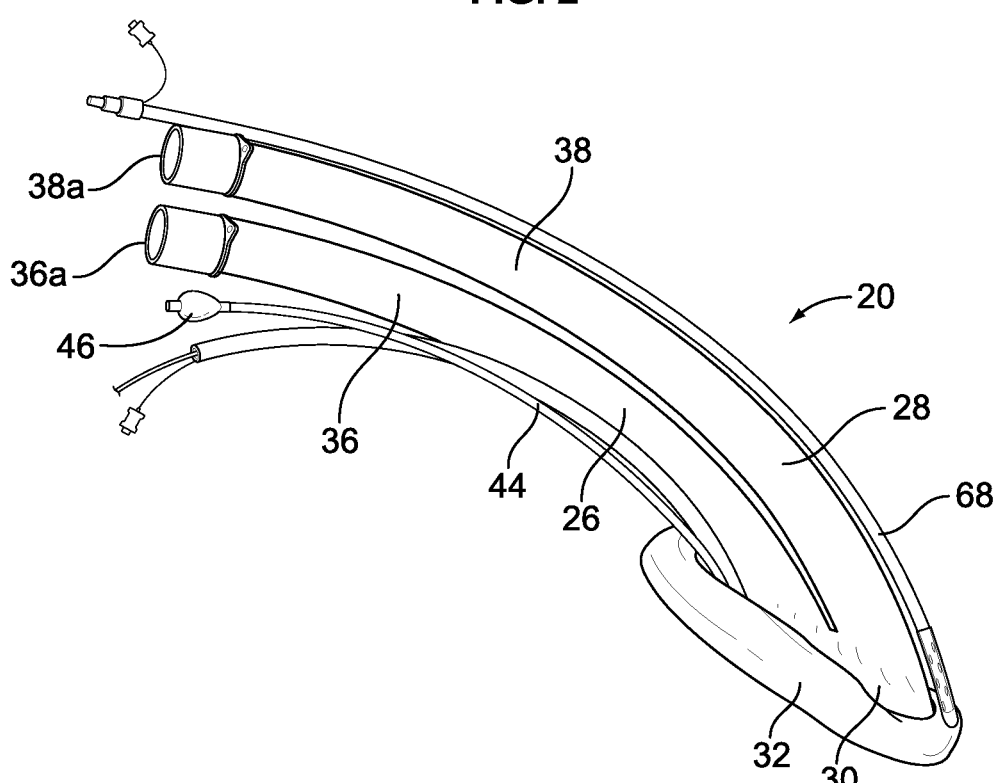
FIG. 3 is an alternate perspective view of the medical device of FIG. 1.
Figure 4:
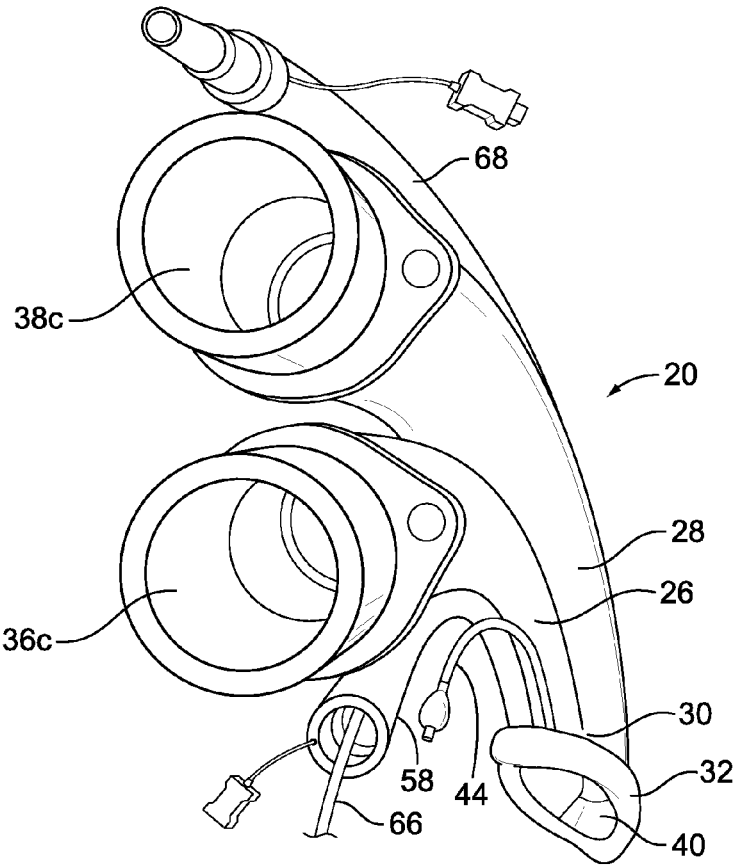
FIG. 4 is yet another alternate perspective view of the medical device of FIG. 1.
Figure 5:
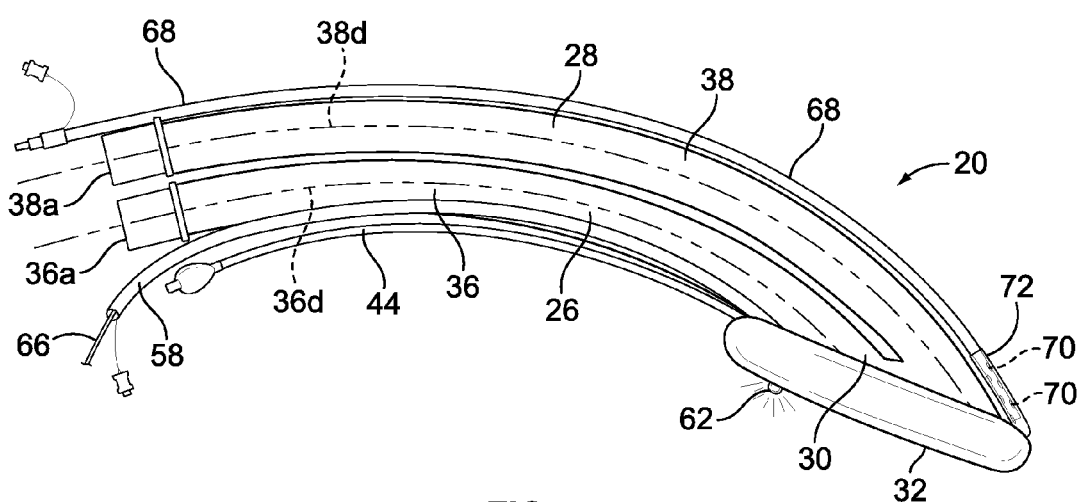
FIG. 5 is a side elevation view of the medical device of FIG. 1.
Figure 6:
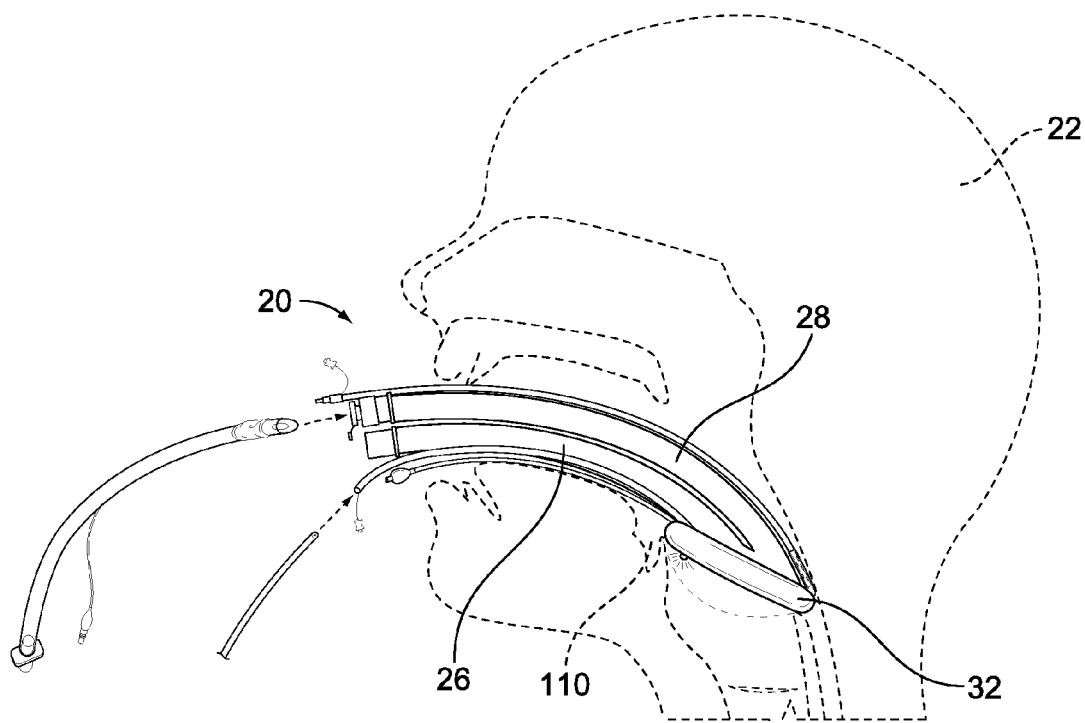
FIG. 6 is a side elevation view of the medical device of FIG. 1 inserted into a patient.
Figure 7:
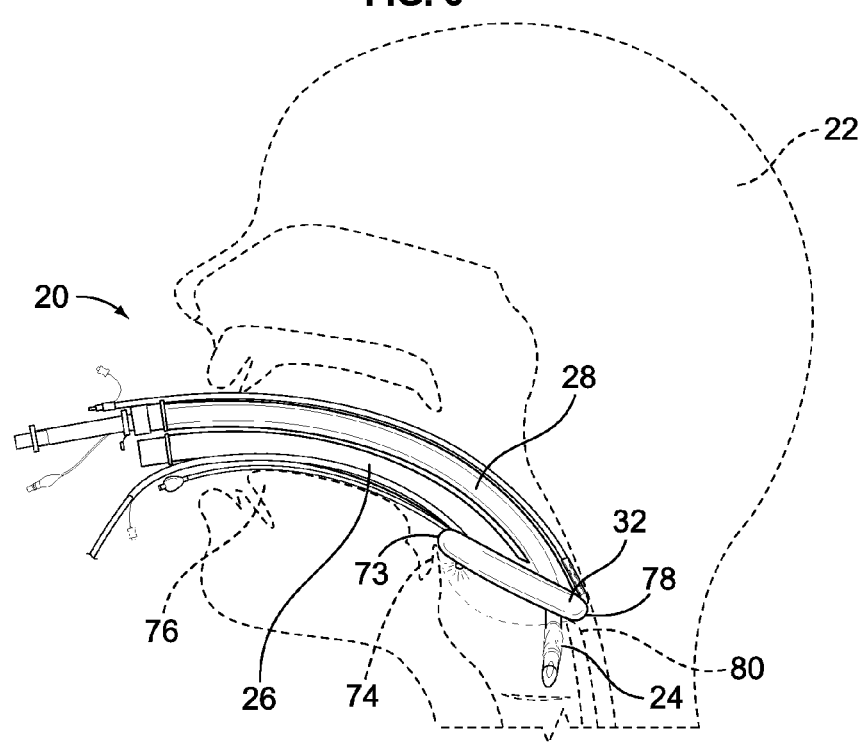
FIG. 7 is a side elevation view of the medical device of FIG. 1 inserted into a patient, and shown with an endotracheal tube inserted therein.

While the invention may be susceptible to embodiment in different forms, there is shown in the drawings, and herein will be described in detail, a specific embodiment with the understanding that the present disclosure is to be considered an exemplification of the principles of the invention, and is not intended to limit the invention to that as illustrated and described herein. Therefore, unless otherwise noted, features disclosed herein may be combined together to form additional combinations that were not otherwise shown for purposes of brevity.

Figure 8:
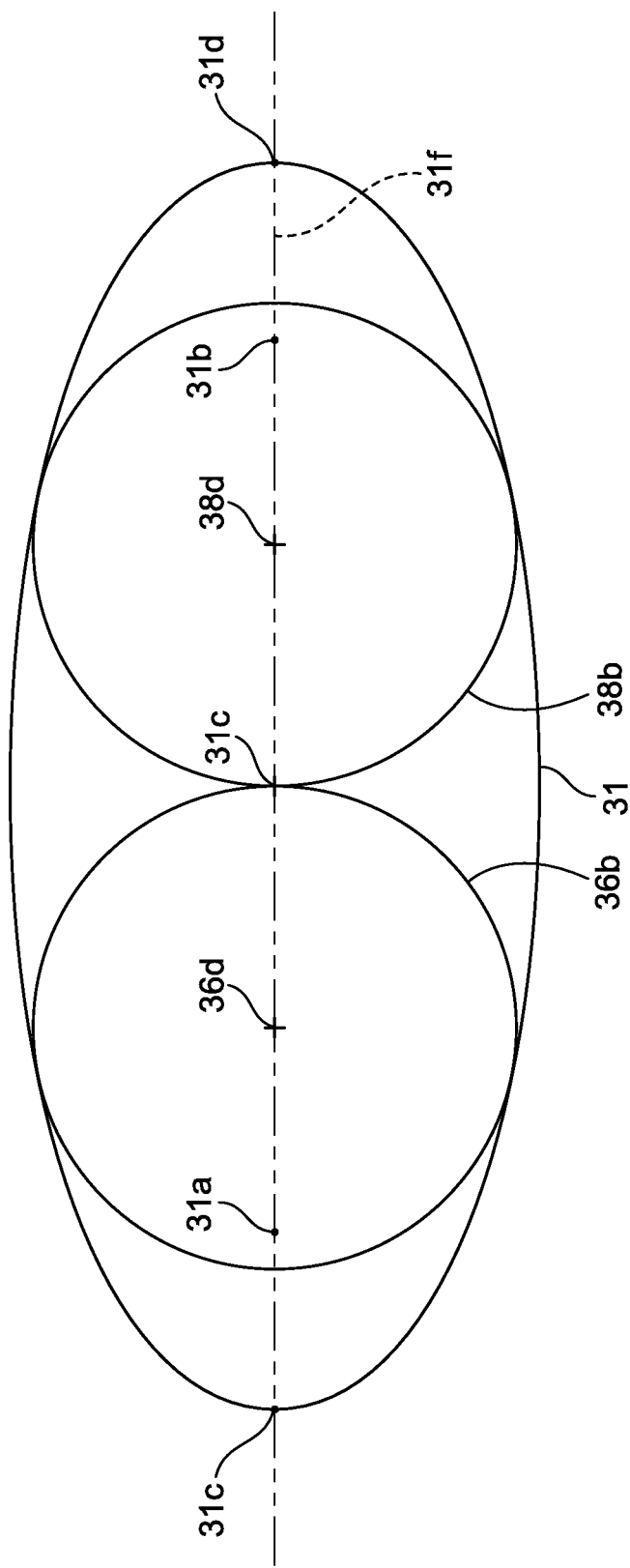
FIG. 8 is a schematic view of the medical device of FIG. 1.
Figure 9:
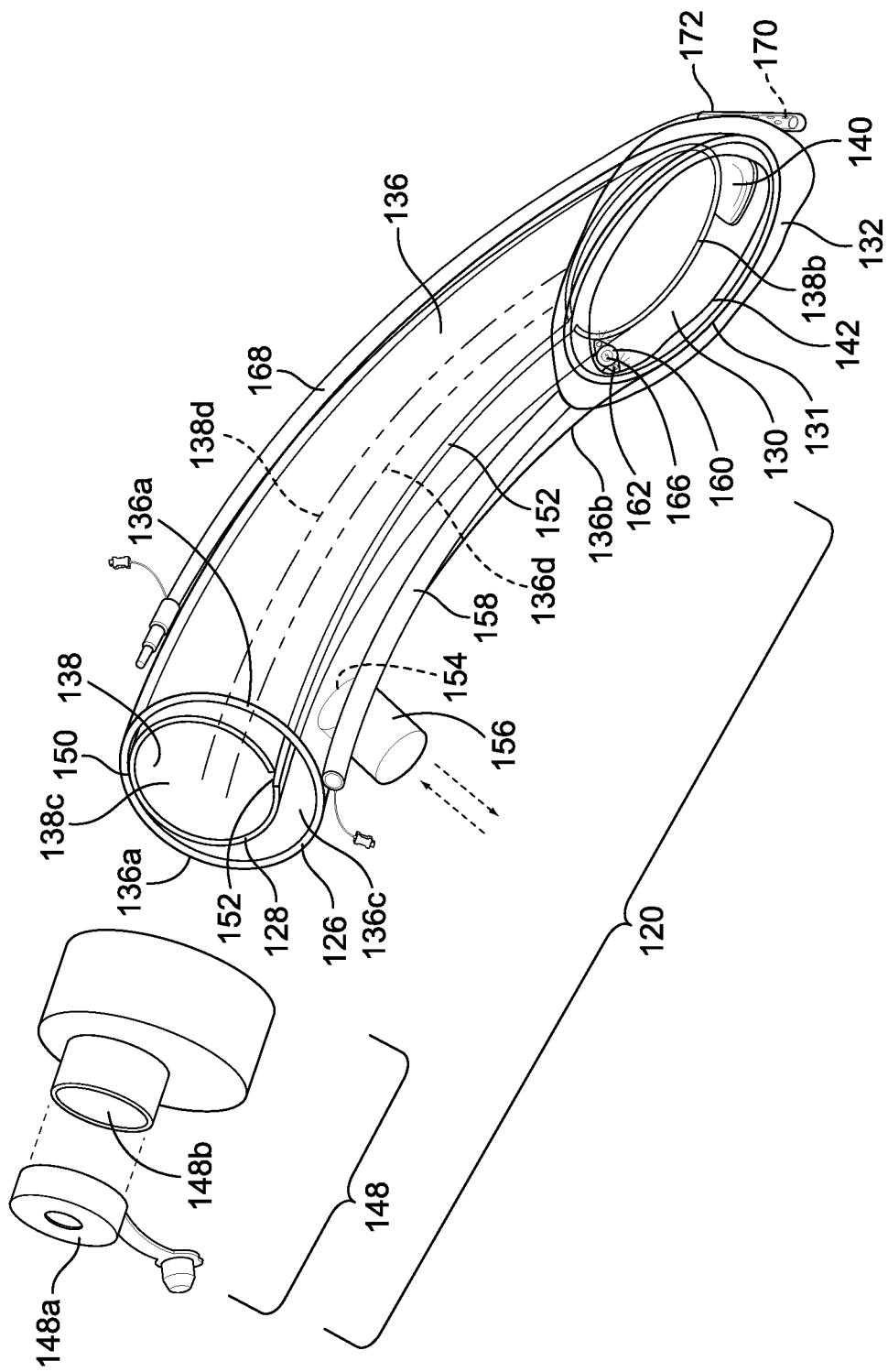
FIG. 9 is a perspective view of an alternate medical device which incorporates the features of the present invention.

FIGS. 1-8 show a first embodiment of a medical device 20 and FIGS. 9/9A and 10 show a second embodiment of a medical device 120. The medical device 20, 120 is inserted into the throat of a patient 22 to open the airway to allow the patient 22 to breathe on his/her own, to allow the patient 22 to breathe with ventilation via a ventilator 23 or for intubating the patient 22 with an endotracheal tube 24. Each medical device 20, 120 is formed of a dual-tube design which includes a ventilating tube 26, 126 and an intubating tube 28, 128 which are connected to a dome 30, 130. A cuff 32, 132, which may inflatable, is attached to the perimeter 31, 131 of the dome 30, 130. While the inflatable cuff 32, 132 is shown and described herein, the inflatable cuff 32, 132 is not necessary, or it may be formed of rubber provided at the end of the tubes 26, 126, 28, 128. The dual-tube design provides the ventilating tube 26, 126 for allowing the patient to breathe on his/her own or for ventilation, and the intubating tube 28, 128 for intubation of the patient 22.

Each medical device 20, 120 includes a camera lumen 58 which is formed by a small diameter flexible plastic tube. The camera lumen 58 has a proximal end and an opposite distal end and a central passageway therethrough. The distal end of the camera lumen 58 has a clear window 60 which is sealed to the camera lumen 58 to close the end of the central passageway. As a result, the camera lumen 58/window 60 are impervious to gases/fluids such that entry of fluids and other matter into the camera lumen 58 is prevented. A pair of LED lights 62 may be formed in the wall of the camera lumen 58 on opposite sides of the window 60. If LED lights 62 are provided in the camera lumen, wires are molded into the camera lumen 58 and extend from the proximal end thereof for connection to a suitable power source. A non-disposable camera 66 can be easily slid into and removed from the sealed camera lumen 58/window 60 combination. Instead of providing separate LED lights 62 in the camera lumen 58, the camera 66 and LED lights 62 (or other source of lighting, including a camera with its own built-in lighting) can be incorporated into a single non-disposable device which is insertable and removeable from the camera lumen 58.

Each medical device 20, 120 includes a transmission lumen 68 for transmitting breath and heartbeat sounds from the patient 22 to the medical professional. The transmission lumen 68 is formed by a small-diameter flexible plastic tube having a central passageway and a series of perforations 70 at its distal end. The perforations 70 are covered by a thin gauge plastic cap 72. When the medical device 20, 120 is seated in the throat of the patient 22, the distal end of the transmission lumen 68 is positioned closest to the esophagus 80 which enables breath and heartbeat sounds to be easily transmitted through the perforations 70 and along the length of the transmission lumen 68 to the medical professional monitoring the patient 22.

Attention is invited to the first embodiment of the medical device 20 shown in FIGS. 1-8 which shows the specifics of the dual-tube design. [0006] Each tube 26, 28 is formed from a cylindrical wall 36, 38 having a proximal open inlet 36a, 38a (at the end closest to the medical professional), an opposite distal open outlet 36b, 38b (at the end furthest away from the medical professional during use of the medical device 20) and a central passageway 36c, 38c extending through the respective tube 36, 38. Each tube 36, 38 has a centerline 36d, 38d which extends from the proximal inlet 36a, 38a to the distal outlet 36b, 38b. The tubes 26, 28 are curved along the length of each tube 26, 28 and the centerlines 36d, 38d are accordingly curved. Each tube 26, 28 has a diameter which is preferably 15 mm, however, each tube 26, 28 may be bigger or smaller, and/or not of equal diameter with respect to each other. Each tube 26, 28 is formed of a relatively stiff but compliant plastics material and is preferably formed by extrusion. The tubes 26, 28 are situated side-by-side and thus the centerlines 36d, 38d of the tubes 26, 28 are parallel to each other. The inlets 36a, 38a generally align with each other, and the outlets 36b, 38b generally align with each other. Proximate to the distal outlets 36b, 38b of the tubes 26, 28, the inner portions of the walls 36, 38 merge together at the dome 30.

The dome 30 is formed of a plastics material like that of the tubes 26, 28. The dome 30 has a ramped surface 40 proximate to the intubating tube 28 which acts as a ramp for the insertion of the endotracheal tube 24 into the throat of the patient 22. The perimeter 31 of the dome 30 distal from the distal ends of the tubes 26, 28 generally forms an ellipse.

The centerlines 36d, 38d of the tubes 26, 28 generally fall along the major axis 31f of the ellipse and are offset from each other, with one centerline 36d proximate to one focus 31a of the ellipse and the other centerline 38d proximate to the other focus 31 b of the ellipse. As schematically shown in FIG. 8, the distal open outlet 36b of the ventilating tube 26 generally aligns with focus 31a and forms a ventilating passageway. The distal open outlet 38c of the intubating tube 28 generally aligns with focus 31 b. The ramped surface 40 is between distal open outlet 38c of the intubating tube 28 and the vertex 31d of the ellipse. The inner portions of the walls 36, 38 preferably generally align with the center 31c of the ellipse. The intubating tube 28 and the ramped surface 40 form an intubating passageway along their lengths. While the distal open outlet 38c of the intubating tube 28 is described and shown as generally aligning with focus 31 b, it is to be understood that the ramped surface 40 can be positioned to generally align with this focus 31 b.

The inflatable cuff 32, if provided, surrounds the perimeter 31 of the dome 30. A central opening 42 is formed by the cuff 32. The inner edge of the cuff 32 is bonded or otherwise suitably secured, such as by ultrasonic welding, to the perimeter 31 of the dome 30. Thus the inner edge of the cuff 32 is generally elliptical. The cuff 32 is preferably formed of a thin, flexible plastics material so that the cuff 32 can be deflated to a low profile for insertion into the patient 22 and can be inflated to seal with the surrounding tissue when the medical device 20 is correctly positioned in the throat of the patient 22 as described herein.

The medical device 20 includes an inflation line 44 which is formed by a small diameter flexible plastic tube. As shown, the inflation line 44 is provided proximate to the ventilating tube 26 at a position farthest from the intubating tube 28. This position is only illustrative and the inflation line 44 can be provided at other locations. The distal end of the inflatable cuff 32 is sealed with the outside of the inflation line 44 so that it opens into the interior of the inflatable cuff 32. The proximal end of the inflation line 44 is attached to a combined inflation indicator balloon and connector 46 which are known in the art. The inflation line 44 can be attached to one of the tubes 26, 28 along its length, if desired. Alternatively, an extruded small-bore lumen (not shown) can be provided within the wall 36, 28 of one of the tubes 26, 28 to provide the inflation line 44.

A cap 48 is provided at the proximal end of the intubating tube 28 for sealing the proximal outlet 38a of the intubating tube 28 when it is not in use. Preferably, the cap 48 is formed of rubber. The cap 48 can have a flip-top, or can be removed from the intubating tube 28, to allow access to the intubating passageway when needed. Other means for sealing the end of the intubating tube 28, while selectively allowing access to the intubating passageway therein, are within the scope of the present invention.

The camera lumen 58 has a distal end which is preferably provided at the vertex 31e of the ellipse between the ventilating tube 26 and the cuff 32. The ventilating tube 26 and the cuff 32 are sealed to the camera lumen 58 by suitable means. Instead of a separate lumen attached to the ventilating tube 26 and the cuff 32, an extruded small-bore lumen can be provided within the wall of the ventilating tube 26, with the window 60 sealed to the end thereof. The camera 66 is preferably provided at the vertex 31 e of the ellipse between the ventilating tube 26 and the cuff 32 as this provides the best angle for viewing the tissues of the patient 22 when the medical device 20 is being inserted. It is to be understood that the camera 66 can be placed in other positions.

The transmission lumen 68 seats against the intubating tube 28 and the distal end of the transmission lumen 68 is attached to the cuff 32 or is attached near the distal outlet 38b of the ventilating tube 26 near the cuff 32, such that the end of the transmission lumen 68 is positioned proximate to the ramped surface 40. When the medical device 20 is seated in the throat of the patient 22, the distal end of the transmission lumen 68 is positioned closest to the esophagus 80 which enables breath and heartbeat sounds to be easily transmitted through the perforations 70 and along the length of the transmission lumen 68 to the medical professional monitoring the patient 22.

In use, the medical professional inserts the medical device 20 through the mouth and into the throat of the patient 22. The intubating tube 28 is closed by the cap 48 at its proximal outlet 38a and is not used. The ventilating tube 26 remains open to allow the patient 22 to breathe on his/her own through the ventilating tube 26 through the open proximal inlet 36a of the ventilating tube 26. The ventilating tube 26 can also be connected to the ventilator 23 to provide assisted breathing to the patient 22. The cuff 32 and the intubating tube 28 slide against the hard palate and then against the soft palate and into the pharynx of the patient 22. The medical device 20 will flex to assume a curved shape to conform to the throat of the patient 22. The medical professional uses the camera 66 to properly guide the medical device 20 into the pharynx. Because the camera 66 provides constant visualization of the tissues during insertion of the medical device 20 into the patient, the medical professional can be assured that the medical device 20 is being properly inserted and positioned in the throat of the patient 22 with limited trauma to the patient 22. The medical professional can see the vocal folds via the camera 66 to ensure proper positioning of the medical device 20 in the patient's throat. Once positioned in the pharynx, one end 73 of the cuff 32 seats against the epiglottis 74 pushing it toward the tongue 76 of the patient 22 and the opposite end 78 of the cuff 32 seats in the esophagus 80. The cuff 32 is then inflated. As a result, the esophagus 80 is blocked by the cuff 32 and the epiglottis 74 is moved out of the way of the ventilating and intubating passageways 36c, 38c. The distal outlets 36b, 38b of the ventilating and intubating passageways 36c, 38c are open to the glottis of the patient 22. During this entire procedure of insertion, the camera 66 provides constant visualization of the tissues during insertion of the medical device 20 into the patient 22. The patient 22 can breathe by airflow through the open ventilating tube 26. Since the camera 66 is constantly operating during insertion and through the entire medical procedure, the medical professional can constantly visually confirm that the patient 22 is breathing. The constant visualization of the laryngeal inlet and the vocal folds of the patient 22 can make earlier diagnoses of issues, for example, but not limited to, secretions, tumors, paralyzed vocal folds, apnea, bleeding, and abnormal anatomy, as well as other potentially harmful effects to the patient 22.

If the medical professional needs to insert an endotracheal tube 24 into the patient 22, the cap 48 on the intubating tube 28 is removed/opened and the endotracheal tube 24 is inserted through the proximal outlet 38a of the intubating tube 28 and through the passageway 36c of the intubating tube 28. The endotracheal tube 24 will contact the ramped surface 40 which properly directs the endotracheal tube 24 into the pharynx. Once the endotracheal tube 24 exits the intubating tube 28 at its distal outlet 38b, the medical professional can see the positioning of the endotracheal tube 24 via the camera 66. The medical professional can thus guide the endotracheal tube 24 through the vocal folds and into the trachea, and inflate the cuff of the endotracheal tube 24, under the constant visualization provided by the camera 66. At times, the medical device 20 may be advanced, pulled back, or turned from side to side, to maintain the proper trajectory through the vocal folds. This is easily accomplished since there is constant visualization of the tissues via the camera 66. In addition, known moveable stylets (not shown) may be used. The ventilator 23 is then disconnected from the ventilating tube 26 and the ventilating tube 26 is capped, or the ventilator 23 remains connected, but turned off.

As a result of the structure of the medical device 20, the intubating tube 28 is located furthest away from the epiglottis 74 when the medical device 20 is positioned within the patient 22. This minimizes the ability of the epiglottis 74 to block the insertion of the endotracheal tube 24 into the trachea in the event that the epiglottis 74 is not seated between the cuff 32 and the tongue 76.

Attention is now invited to the second embodiment of the medical device 120 shown in FIGS. 9 and 10 which shows the specifics of the dual-tube design.

Each tube 126, 128 is formed from a cylindrical wall 136, 138 having a proximal open inlet 136a, 138a (at the ends closest to the medical professional), an opposite open distal outlet 136b, 138b (at the ends furthest away from the medical professional during use of the medical device 120) and a central passageway 136c, 138c extending through the respective tube 126, 128. Tube 128 is shown in full line in FIG. 9 to illustrate the construction of the tube 128 (of course, in practice, tube 126 may be opaque such that tube 128 would not be visible along its length). The outlets 136b, 138b generally align with each other. Each tube 126, 128 has a centerline 136d, 138d which extends from the proximal inlet 136a, 138a to the distal outlet 136b, 138b. The tubes 126, 128 are curved along the lengths thereof and the centerlines 136d, 138d are accordingly curved. Each tube 126, 128 is formed of a relatively stiff but compliant plastics material and is preferably formed by extrusion. Tube 126 forms the ventilating tube, however, tube 128 is also used in the ventilating process as described herein. Tube 128 forms the intubating tube.

The intubating tube 128 is positioned within the ventilating tube 126. A portion of the wall 136 of the ventilating tube 126 is preferably connected to the intubating tube 128, as shown in FIG. 9, along a junction 150 to affix the tubes 126, 128 together and to prevent the intubating tube 128 from moving around within the ventilating tube 126. The centerlines of the tubes 126, 128 are parallel to each other. The ventilating tube 216 has a diameter which is preferably 20 mm, and the intubating tube 128 has a diameter which is preferably 10 mm.

The intubating tube 128 has an elongated slit 152 along its length opposite to the junction 150 to allow for gas communication between the passageway 136c of the ventilating tube 126 and the passageway 138c of the intubating tube 128. The slit 152 can extend the entire length of the intubating tube 128 as shown, or can extend along a portion of the length of the intubating tube 128.

The ventilating tube 126 has a ventilating port 154 in its wall 136 proximate to, but spaced from, the proximal open inlet 136a thereof. The ventilating port 154 is preferably proximate to the slit 152 in the intubating tube 128. A connector tube 156 is formed around the ventilating port 154. The connector tube 156 may be integrally formed with the ventilating tube 126, or may be a separate component which is sealed to the ventilating tube 126 by known means.

The dome 130 is formed of a plastics material like that of the tubes 126, 128. The dome 130 is formed at the distal outlet 136b of the ventilating tube 126. The dome 130 has a ramped surface 140 which connects to the intubating tube 128 to act as a ramp for the insertion of the endotracheal tube 24 into the throat of the patient 22 as described herein. The perimeter 131 of the dome 30 distal from the distal ends of the tubes 126, 128 generally forms an ellipse.

The inflatable cuff 132 surrounds the perimeter 131 of the dome 130. A central opening 142 is formed by the cuff 132. The inner edge of the cuff 132 is bonded or otherwise suitably secured, such as by ultrasonic welding, to the perimeter 131 of the dome 130. Thus the inner edge of the cuff 32 is generally elliptical. The cuff 132 is preferably formed of a thin, flexible plastics material so that the cuff 132 can be deflated to a low profile for insertion into the patient's throat and can be inflated once properly positioned to seal with the surrounding tissue when the medical device 120 is correctly positioned in the throat of the patient 22 as described herein.

The centerlines 136d, 138d of the tubes 126, 128 generally fall along the major axis 31f of the ellipse and are offset from each other. As schematically shown in FIG. 10, the distal open outlet 136b of the ventilating tube 126 generally aligns with both foci 31a, 31b as this ventilating tube 126 is large. The distal open outlet 138c of the intubating tube 128 generally aligns with one focus 31b. The ramped surface 140 is between distal open outlet 136c of the ventilating tube 128 and the vertex 31d of the ellipse. The intubating tube 128 and the ramped surface 140 form an intubating passageway.

The medical device 120 includes an inflation line like that of the first embodiment (not shown in FIG. 8) and therefore, the specifics are not repeated herein. Like elements are denoted by like reference numerals with the elements of the second embodiment being denoted with reference numerals in the one-hundreds.

A cap 148 attaches to the proximal inlet 136a of the ventilating tube 126 to prevent access to the open proximal outlet 138a of the intubating tube 128 when the endotracheal tube 24 is not being used. Preferably, the cap 148 is formed of rubber. The cap 148 can have a flip-top as shown to allow access to the intubating passageway 138c, or can be removed from the ventilating tube 126 to allow access to the intubating passageway 138c. Other means for sealing the end of the ventilating tube 126, while selectively allowing access to the intubating passageway 138c, are within the scope of the present invention.

The transmission lumen 68 seats against the ventilating tube 126 and the distal end of the transmission lumen 68 is either attached to the cuff 132 or is attached near the distal outlet 138b of the ventilating tube 126 near the cuff 132. When the medical device 120 is seated in the throat of the patient 22, the distal end of the transmission lumen 68 is positioned closest to the esophagus 80 which enables breath and heartbeat sounds to be easily transmitted through the perforations 170 and along the length of the transmission lumen 68 to the medical professional monitoring the patient 22.

The distal end of the camera lumen 58 is preferably provided at the vertex 31e of the ellipse between the ventilating tube 126 and the cuff 132 which are sealed thereto. Alternatively, an extruded small-bore lumen can be provided within the wall of the ventilating tube 126, with the window 60 sealed to the end thereof. The camera 66 is preferably provided at the vertex 31 e of the ellipse between the ventilating tube 126 and the cuff 132 as this provides the best angle for viewing the tissues of the patient 22 when the medical device 120 is being inserted. It is to be understood that the camera 66 and camera lumen 58 can be placed in other positions.

In use, the medical professional inserts the medical device 120 through the mouth and into the throat of the patient 22. The open ventilating tube 126 allows the patient 22 to breathe on his/her own through the connector 156 attached to the ventilating tube 126. The ventilating tube 126 can also be connected to the ventilator 23 to provide assisted breathing to the patient 22. The cuff 132 and the ventilating tube 126 slide against the hard palate and then against the soft palate and into the pharynx of the patient 22. The medical device 120 will flex to assume a curved shape to conform to the throat of the patient 22. The medical professional uses the camera 66 to properly guide the medical device 120 into the pharynx. Because the camera 66 provides constant visualization of the tissues during insertion and the entire time that the medical device 120 is in the patient 22, the medical professional can be assured that the medical device 120 is being properly inserted and maintained. The medical professional can see the vocal folds via the camera 66 to ensure proper positioning of the medical device 120 in the patient's throat. Since the camera 66 is constantly operating, the medical professional can constantly visually confirm movement of the vocal folds to be assured that the patient 22 is breathing. Once positioned in the pharynx, the proximal end of the cuff 132 seats against the epiglottis 74 pushing it toward the tongue 76 of the patient 22 and the distal end of the cuff 132 seats in the esophagus 80. The cuff 132 is then inflated. As a result, the esophagus 80 is blocked by the cuff 132 and the epiglottis 74 is moved out of the way of the ventilating and intubating passageways 136c, 138c. The distal outlets 136b, 138b of the intubating tube 126 and the ventilating tube 128 are open to the glottis of the patient 22. During this entire procedure, the camera 66 provides constant visualization of the tissues during insertion of the medical device 120 into the patient 22 and continues throughout the entire medical procedure. The constant visualization of the laryngeal inlet and the vocal folds of the patient 22 can make earlier diagnoses of issues, for example, but not limited to, secretions, tumors, paralyzed vocal folds, apnea, bleeding, and abnormal anatomy, as well as other potentially harmful effects to the patient 22.

The patient can breathe by airflow through the connector 56/ventilating tube 126. Air can also flow through the slit 152 and through the intubating tube 128 to the patient 22.

If the medical professional needs to insert an endotracheal tube 24 into the patient 22, the cap 148 is removed/opened (opened via removing the plug 148a on the cap 148 to open the passageway 148b in the cap 148) to allow access to the proximal outlet 138a of the intubating tube 128 and the endotracheal tube 24 is inserted through the proximal outlet 138a and through the intubating passageway 138c. The endotracheal tube 24 will contact the ramped surface 140 which properly directs the endotracheal tube 24 into the pharynx. Once the endotracheal tube 24 exits the intubating tube 28, the medical professional can see the positioning of the endotracheal tube 24 via the camera 66. The medical professional can thus guide the endotracheal tube 24 through the vocal folds and into the trachea, and then inflate the cuff of the endotracheal tube 24, under the constant visualization provided by the camera 66. At times, the medical device 120 may be advanced, pulled back, or turned from side to side, to maintain the proper trajectory through the vocal folds. In addition, known moveable stylets (not shown) may be used. The ventilator 23 is then disconnected from the ventilating tube 26 and the connector 156 may be capped (although it can be left open since the endotracheal tube 24 is in place), or the ventilator 23 can remain connected, but turned off.

Figure 9A:
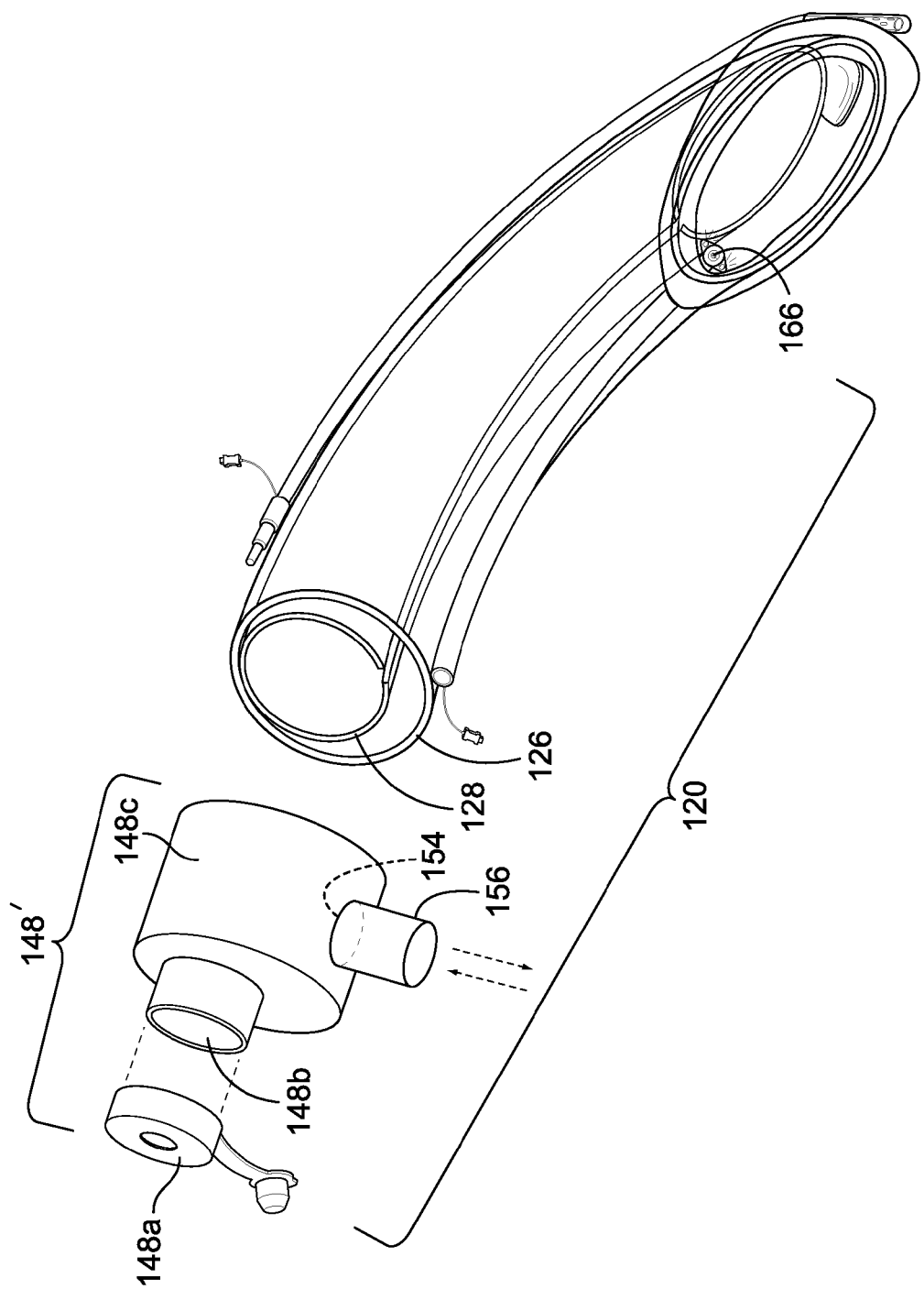
FIG. 9A is a perspective view of a modification to the medical device of FIG. 9.
Figure 12:
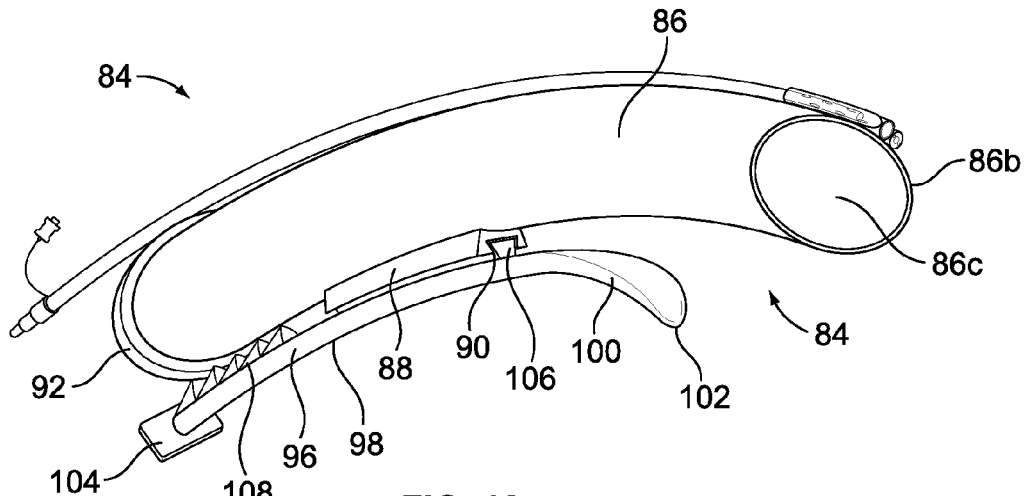
FIG. 12 is a perspective view of an airway assist device which incorporates the features of the present invention for use with the medical devices of FIGS. 1 and 9 and 10.
Figure 13:
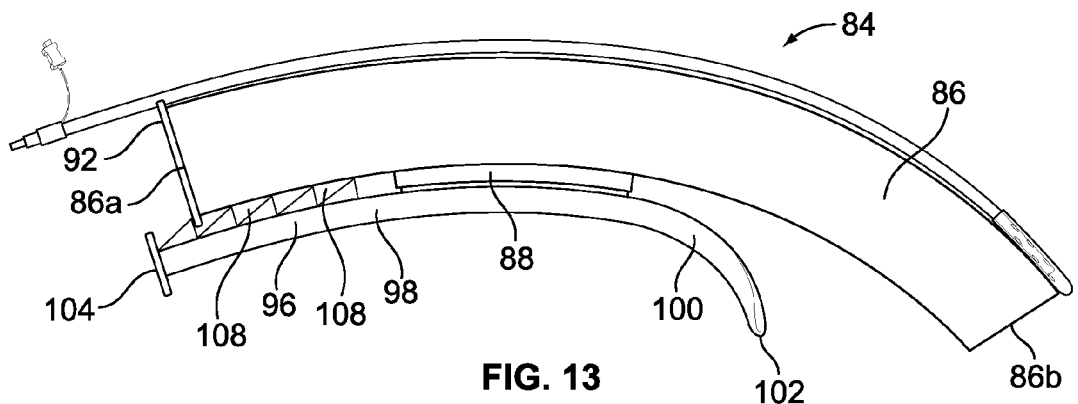
FIG. 13 is a side elevation view of the airway assist device of FIG. 12.
Figure 14:
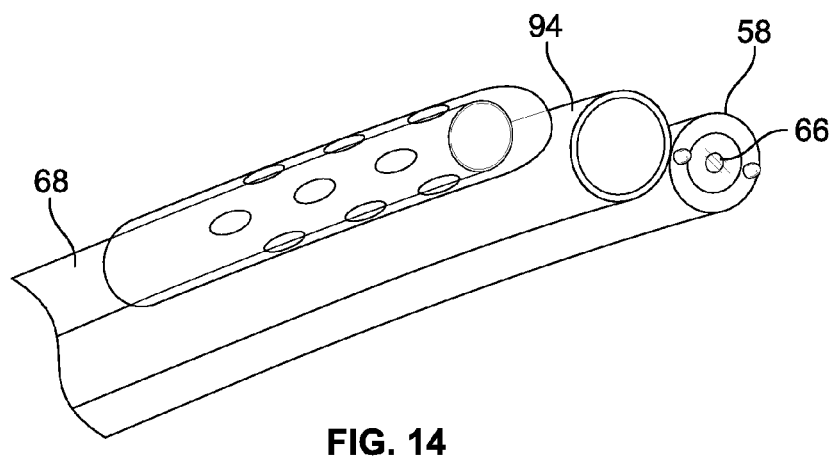
FIG. 14 is a perspective view of the lumens which form part of the airway assist device of FIG. 12.
Figure 15:
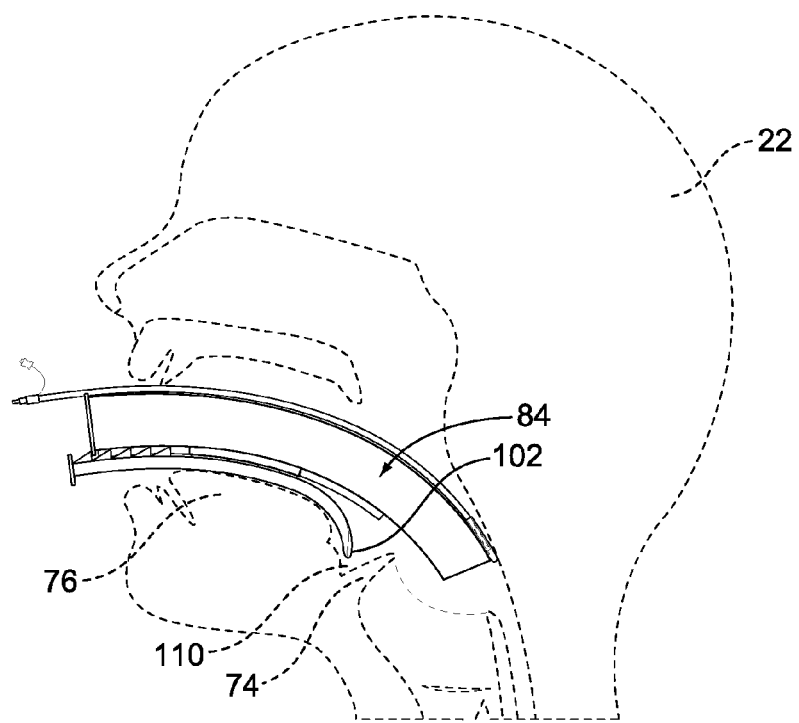
FIGS. 15 and 16 are side elevation views of the airway assist device of FIG. 12 inserted into a patient.
Figure 16:
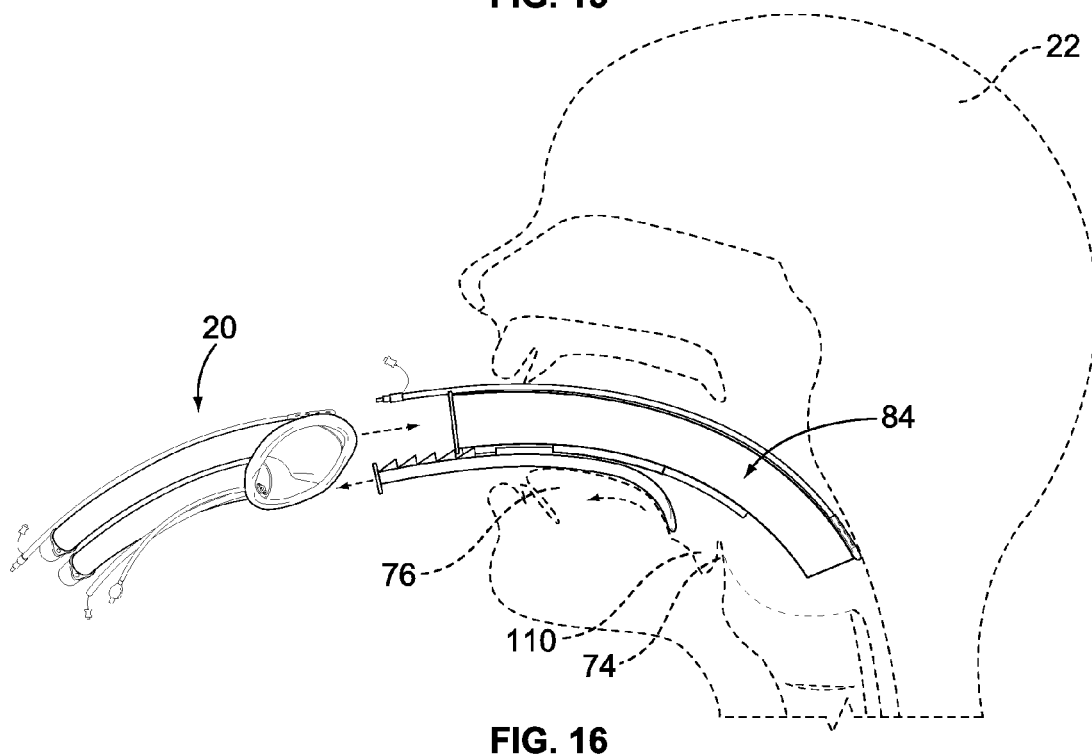
Figure 19:
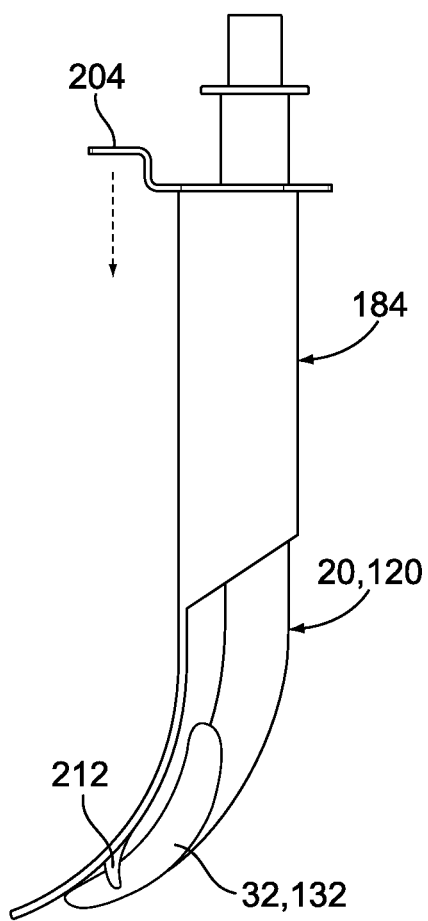
FIGS. 19 and 20 are side elevation views of the airway assist device of FIG. 17 with a medical device mounted therein.
Figure 20:
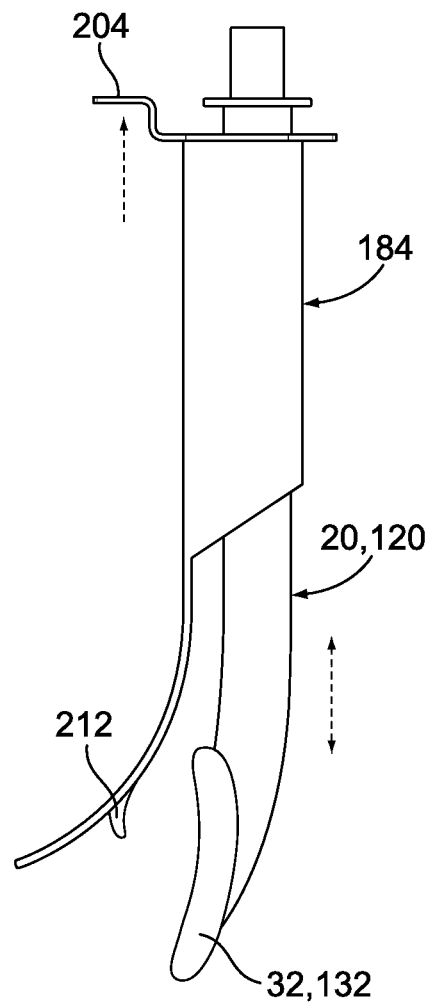
Figure 21:
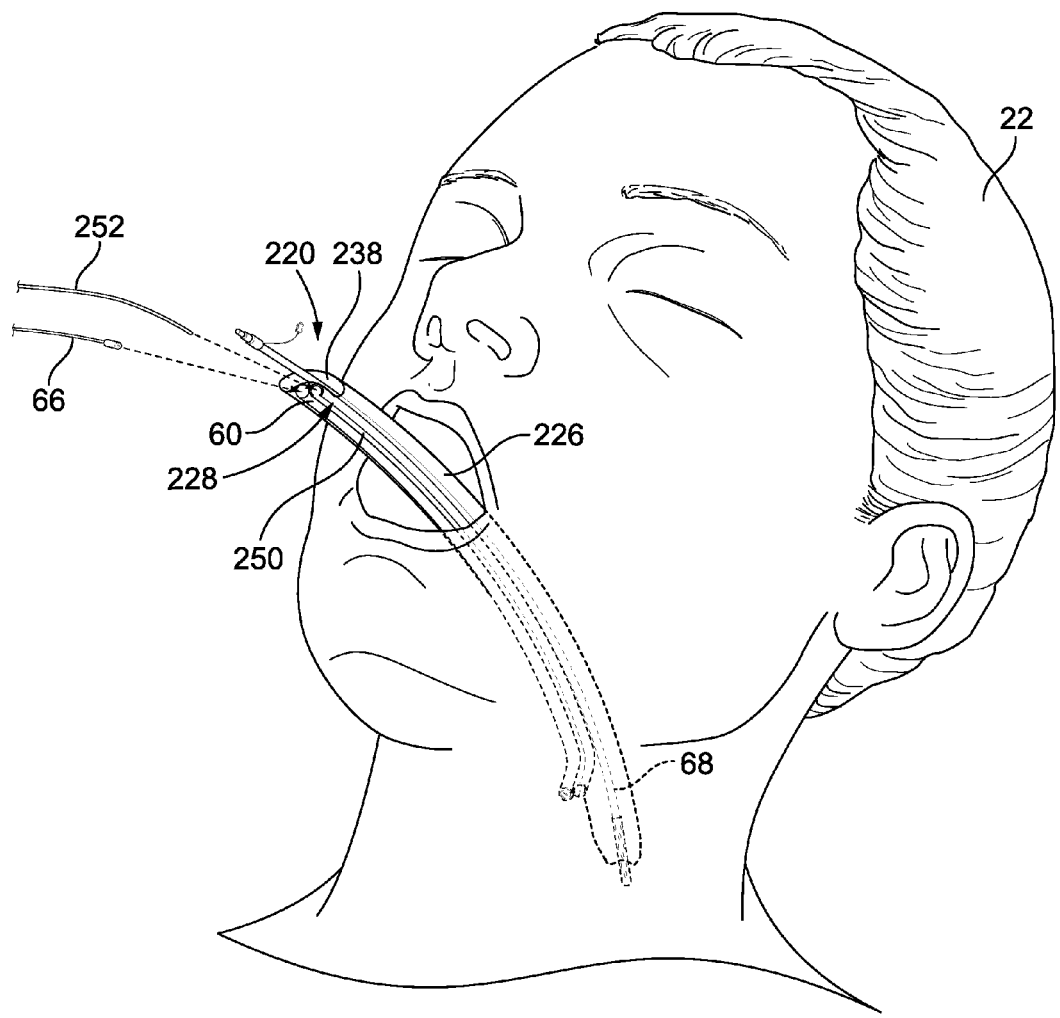
FIG. 21 is a perspective view of another medical device which incorporates the features of the present invention inserted into a patient.
Figure 22:
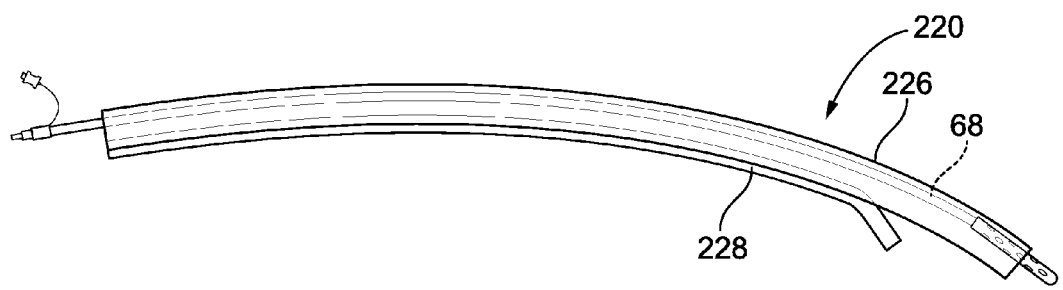
FIG. 22 is a side elevation view of the medical device of FIG. 21.

In this embodiment of the medical device 120, the ventilating port 154 and connector tube 156 can be moved from the tube 126 to a modified cap 148' as shown in FIG. 9A (like that=of FIG. 9, tube 128 is shown in full line in FIG. 9A to illustrate the construction of the tube 128 (of course, in practice, tube 126 may be opaque such that tube 128 would not be visible along its length)). This modified cap 148' allows for ventilation (via ventilation port 56/connector tube 154), intubation (intubation is achieved by removing the plug 148a on the cap 148' to open the passageway 148b in the cap 148'), and connection to the tube 128. The skirt 148c of the cap 148 is longer than the skirt of the cap 148 to accommodate the ventilation port 156, while still allowing the cap 148' to be connected to the tube 128.

The intubating tube 128 is located furthest away from the epiglottis 74 when the medical device 120 is inserted. This minimizes the ability of the epiglottis 74 to block the insertion of the endotracheal tube 24 into the trachea of the patient 22 in the event that the epiglottis 74 is not seated between the cuff 132 and the tongue 76.

The dual tubes 26/126, 281128 thus provide the ability for a patient 22 to breathe on his/her own, to breathe under ventilation via the ventilator 23, or to be intubated using the endotracheal tube 24. The endotracheal tube 24 can be removed from the intubating tube 28, 128 and the intubating tube 28, 128 capped, and the patient 22 can return to breathing on his/her own or under ventilation through the ventilating tube 26, 126 without removal of the medical device 20, 120 from the patient 22. If the patient 22 becomes distressed or if circumstances dictate, the endotracheal tube 24 can be reinserted into the intubating tube 28, 128. This provides great flexibility for the medical professional to keep the patient's airway open, to constantly visually verify that the patient's airway is open during the entire medical procedure, and to constantly verify by hearing that the patient's airway is open during the entire procedure.

The transmission lumen 68 is positioned proximate to the esophagus 80 which is the location closest to the lungs and heart of the patient 22. This enables breath and heart sounds to be easily transmitted along the transmission lumen 68.

The medical device 20, 120 is intended to be in the patient 22 during the entire medical procedure. The video information from the camera 66 and the information from the transmission lumen 68 are transmitted to a microprocessor 82, FIG. 11, via appropriate means, such as wires, wireless, Bluetooth, etc., which in turn can transmit the information to another computer, mobile devices, a mobile station and the like, via appropriate means, such as wires, wireless, Bluetooth, etc., and then this information can be accessed by appropriate personnel. This microprocessor 82 can be on-site where the procedure is being performed or can be remote from the procedure site. For example, the information can be supplied to the nurses' station and the nurse on duty will be able to instantly know if the patient 22 is breathing by the visual confirmation that the vocal folds are opening and closing and by hearing breath and heart sounds. The medical professional will be able to interpret the depth of anesthesia by looking at the rhythmic movement of the vocal folds as well as other diagnoses previously mentioned. Other medical personnel can be hundreds of miles away and still be able to monitor, advise, confirm, and diagnose without the patient 22 being in close physical proximity to that medical personnel. Since the camera 66 is constantly operating, medical personnel can tell at any time if the patient 22 is properly ventilated/intubated and is breathing.

If desired, the medical device 20, 120 can be removed once the endotracheal tube 24 is properly positioned because the intubating passageway 38c, 138c is sufficiently large to slide over the endotracheal tube 24 without dislodging the endotracheal tube 24 from the patient's throat.

A temperature sensor (not shown) can also be incorporated into the medical device 20, 120 for providing temperature information to the appropriate personnel via the microprocessor 82.

The medical device 20, 120 is disposable. Since the camera 66 is removed from the medical device 20, 120 before disposal, an expensive component of the medical device 20, 120 is reusable. While the lights 62 are described as being provided in the medical device 20, 120, it is possible for the lights 62 to be built into the camera 66.

FIGS. 12-16 show a first embodiment of an airway assist device 84 and FIGS. 17-20 show a second embodiment of an airway assist device 184, each of which are used in combination with the medical device 20, 120. The airway assist device 84, 184 can be used to manipulate the position of the patient's epiglottis 74 and tongue 76 to further ensure that the epiglottis 74 and tongue 76 are moved out of the way of the ventilating and intubating passageways 36c, 136c, 38c, 138c and to minimize the chance of blockage of the passageways 36c, 136c, 38c, 138c by the epiglottis 74. These airway assist devices 84, 184 allow first responders, for example, paramedics, an easier way to provide patency to the airway of the patient 22, and to easily advance the medical device 20, 120 under constant visualization by the camera 66.

Attention is invited to the airway assist device 84 shown in FIGS. 12-16. The airway assist device 84 is formed from an airway holder 86 and a tongue positioner 96.

The airway holder 86 is formed of a cylindrical tube which has a central passageway 86c extending from a proximal end 86a thereof to a distal end 86b thereof. The central passageway 86c has a large enough diameter to allow the medical device 20, 120 to pass therethrough. The airway holder 86 is preferably curved in the same shape as the medical devices 20, 120.

An elongated mounting extension 88 extends from the airway holder 86. The mounting extension 88 has a dovetail opening 90 extending along the length thereof. Alternatively, the wall of the airway holder 86 could be thickened and the dovetail opening 90 formed therein. A collar 92 is provided at the proximal end 86a of the airway holder 86 and extends perpendicularly therefrom.

The airway assist device 84 includes a camera lumen 58 for housing a camera 66 and a transmission lumen 68 attached to the outer surface of the airway holder 86 at a position which is diametrically opposed to the mounting extension 88. The camera lumen 58, the camera 66 and the transmission lumen 68 are identical to those shown in the medical devices 20, 120 and the specifics are therefore not repeated. A lumen 94 for housing a temperature sensor is also provided (such a lumen 94 and temperature can be provided with the medical devices 20, 120). As shown, the lumens 58, 68, 94 are positioned side-by-side and attached to the airway holder 86 by suitable means. The lumens 58, 68, 94 can be integrally formed with the airway holder 86.

The tongue positioner 96 is slidably received in the mounting extension 88. The tongue positioner 96 has an elongated body 98 which is curved and has a distal end 100 which has a radius which is substantially greater than the radius at which the body 98 is curved. The edge 102 of the distal end 100 is preferably arcuate. A handle 104 is provided at the proximal end of the body 98 which enables a medical professional to grasp the tongue positioner 96. The tongue positioner 96 is preferably formed of a rigid plastic. The distal end 100 may be covered with a soft material, such as silicone. A dovetail protrusion 106 extends outwardly from the body 98 and seats within the dovetail slot 90 in the mounting extension 88.

A series of spaced apart ratchet teeth 108 extend outwardly from the body 98 proximate to the handle 104. The teeth 108 are capable of engaging with the collar 92 to hold the position of the tongue positioner 96 proximally and distally relative to the airway holder 86.

In use, the medical professional inserts the airway assist device 84 into the mouth of the patient 22. The airway holder 86/lumens 58, 68, 94 28 slide against the hard palate and then against the soft palate and partially into the pharynx of the patient 22 until the distal end 100 of the airway assist device 84 enters into the vallecula 110 and the edge 102 engages the tissues of the patient 22. The tongue positioner 96 may slide along the patient's tongue 76. The camera 66 on the airway assist device 84 allows the medical professional to see the tissues and determine the proper positioning of the airway assist device 84. Once properly positioned in the vallecula 110, the medical professional pulls on the handle 104 to move the tongue positioner 96 proximally relative to the medical device tube 86. The distal end 100 engages the patient's tongue 76 and pulls the tongue 76 proximally toward the outside of the mouth of the patient 22. As a result, the epiglottis 74 is also pulled proximally to further open the airway of the patient 22. The teeth 108 ratchet on the collar 92 of the airway holder 86 and prevent the tongue positioner 96 from moving distally relative to the airway holder 86. During this procedure, the patient 22 can breathe through the central passageway 86c of the airway holder 86.

When the epiglottis 74 is pulled proximally, the medical professional inserts the medical device 20, 120 into the central passageway 86c of the airway assist device 84 and properly positions the medical device 20, 120 in the patient's throat as described herein.

After insertion of the medical device 20, 120, the medical professional releases the 14 patient's tongue 76 by pulling the tongue positioner 96 away from the airway holder 86 to disengage the teeth 108 from the collar 92. The rigid plastic of the tongue positioner 96 has enough flexibility to allow the elastic deformation of the tongue positioner 96. Once the teeth 108 are disengaged from the collar 92, the medical professional pushes the tongue positioner 96 distally relative to the airway holder 86 to cause the tongue 76 of the patient to move rearwardly into the patient's mouth. Thereafter, the airway assist device 84 can be removed from the patient's mouth by sliding it over the medical device 20, 120.

Attention is invited to the airway assist device 184 shown in FIGS. 17-20. With this embodiment, the ventilating tube 26, 126 has a collar 192 at its proximal end which extends=perpendicularly from the ventilating tube 26, 126.

The airway assist device 184 includes a tongue positioner 196 having an elongated body 198 which is curved and has a distal end 200 which has a radius which is substantially greater than the radius at which the body 198 is curved. The edge 202 of the distal end 200 is preferably arcuate. A handle 204 is provided at the proximal end of the body 198 which enables a medical professional to grasp the tongue positioner 196. The tongue positioner 196 is preferably formed of a rigid plastic. The distal end 200 may be covered with a soft material, such as silicone.

The airway holder 186 includes a pair of tabs 212 and a pair of arms 216.

The tabs 212 extend upwardly from the distal end 200 proximate to, but spaced from, the edge 202. Each tab 212 is curved and aligned with each other such that the ends of the tabs 212 face each other. As a result, a space 214 is formed between each of the tabs 212 and the distal end 200. This space 214 has a dimension which is approximately equal to the inflatable cuff 32, 132 in the deflated condition. The tabs 212 are spaced apart from each other a distance which is generally equal to the width of the inflatable cuff 32, 132.

The arms 216 extend upwardly from the body 198. Each arm 216 is generally L-shaped, with a first section 216a extending perpendicularly from the body 198 and second sections 216b extending perpendicularly from the first section 216a. The ends of the second sections 216b are spaced apart from each other to form a slot 218. The slot 218 has a width which is slightly less than the diameter of the medical device 20, 120. The arms 216 and the body 198 form a medical device receiving passageway 186. A tooth 208 extends upwardly from the proximal end of the body 198 between the arms 216. The tooth 208 is capable of engaging with the collar 192.

In use, the medical professional first inserts the medical device 20, 120 into the airway assist device 184 by inserting the medical device 20, 120 through the slot 218 and into the central passageway 186 of the airway assist device 184. The arms 216 can elastically flex outwardly as necessary to allow the medical device 20, 120 to pass through the slot 218. The cuff 32, 132 seats underneath the tabs 212 such that the cuff 32, 132 is sandwiched between the tabs 212 and the distal end 200.

The medical professional then inserts the combined medical device 20, 120/airway assist device 184 into the mouth of the patient 22. The airway assist device 184 is sandwiched between the medical device 20, 120 and the tongue 76 of the patient 22. The medical device 20, 120 slides against the hard palate and then against the soft palate and partially into the pharynx of the patient 22 until the distal end 100 of the airway assist device 84 enters into the vallecula 110 and the arcuate edge 202 engages the tissues of the patient 22. The camera 66 on the medical device 20, 120 provides visual means to the medical professional to properly insert the distal end 200 into the vallecula 110. The tongue positioner 196 may slide along the patient's tongue 76. Once the distal end 200 is positioned in the vallecula 110, the medical professional pulls on the handle 204 to move the tongue positioner 196 proximally relative to the medical device 20, 120. The distal end 200 engages the tongue 76 and pulls the tongue 76 proximally toward the outside of the mouth of the patient 22. As a result, the epiglottis 74 is also pulled proximally. During this procedure, the patient 22 can breathe through the medical device 20, 120 as described herein.

When the epiglottis 74 is pulled proximally, the medical professional then pulls the medical device 20, 120 proximally to release the cuff 32, 132 from the tabs 212. The freed medical device 20, 120 then can be finally inserted with the distal end of the medical device 20, 120 in the upper esophagus 80 of the patient 22 as discussed above.

After insertion of the medical device 20, 120, the medical professional releases the patient's tongue 76 by pushing the tongue positioner 196 distally into the patient's mouth to cause the tongue 76 of the patient to move rearwardly. Thereafter, the airway assist device 184 can be removed from the patient's mouth by sliding it over the medical device 20, 120.

While the cuff 32, 132 has been described as inflatable, the cuff 32, 132 can be formed of a soft material, such as silicone, which will readily seal with the tissues in the glottis when the medical device 20, 120 is seated therein.

FIGS. 21-25E show a medical device 220 which is inserted into the throat of a patient 22 to determine the status of the internal membranes of the patient 22 and to provide a means for intubating the patient 22 with an endotracheal tube 24. The medical device 220 includes an esophageal tube 226 and an intubating tube 228 which are connected together. The esophageal tube 226 is used to monitor breath sounds of the patient 22, and the intubating tube 228 is used for intubation of the patient 22 using the endotracheal tube 24 as described herein.

Figure 23:
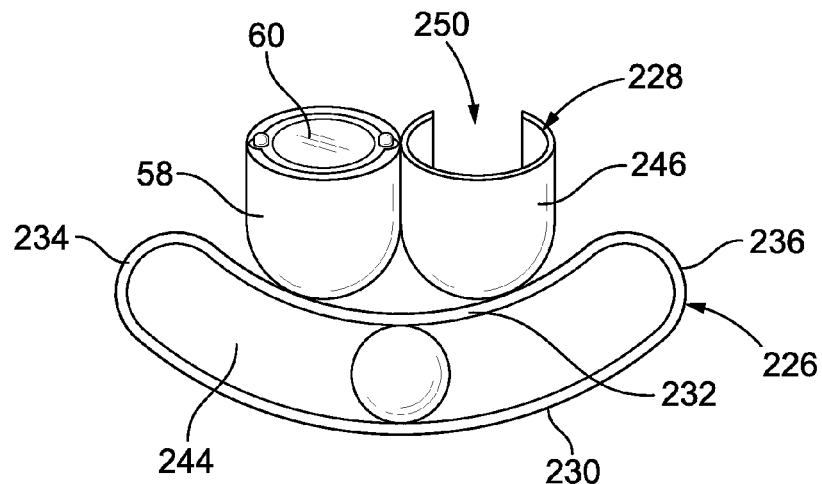
FIG. 23 is an end elevation view of the medical device of FIG. 21.
Figure 24:
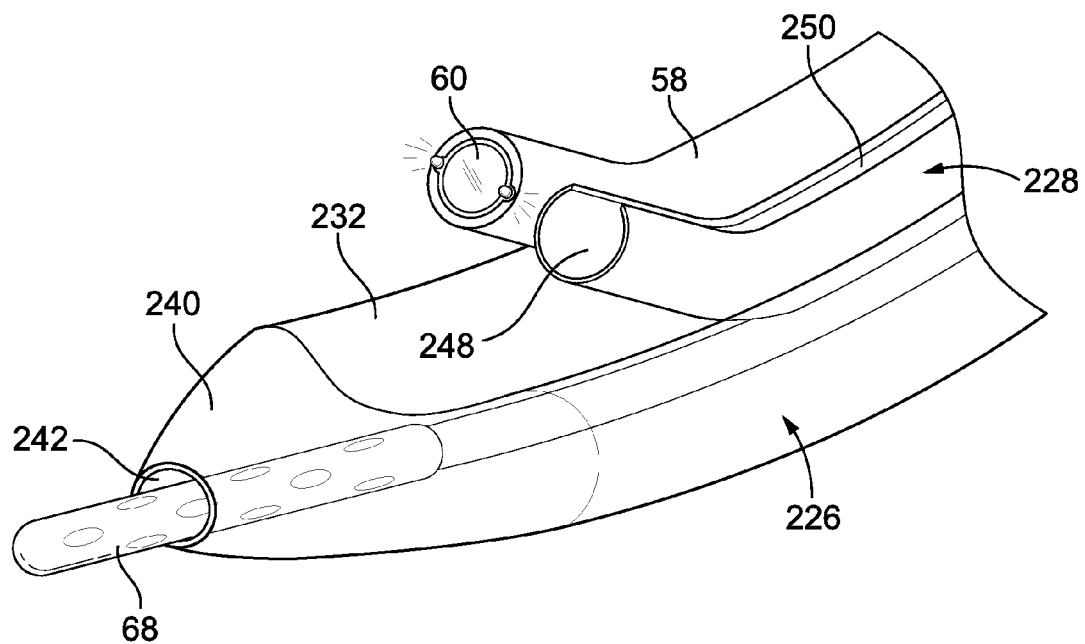
FIG. 24 is alternate perspective view of the medical device of FIG. 21.
Figure 25A:
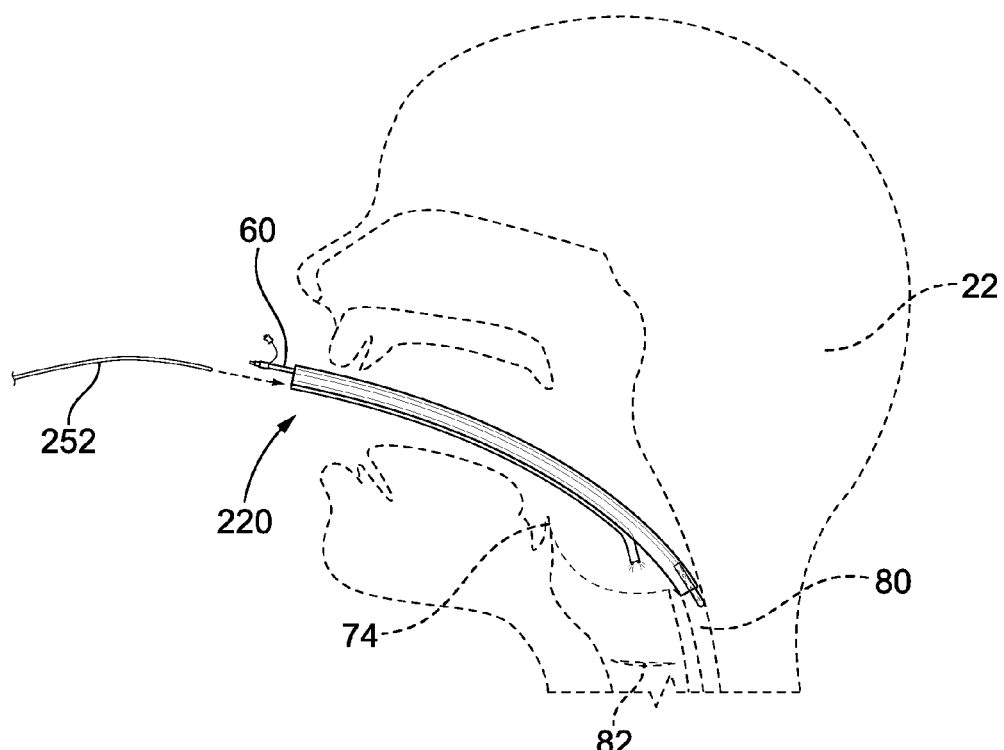
FIGS. 25A-25E are side elevation views of the medical device of FIG. 21 being inserted into a patient, and being used with a stylet and an endotracheal tube.
Figure 25B:
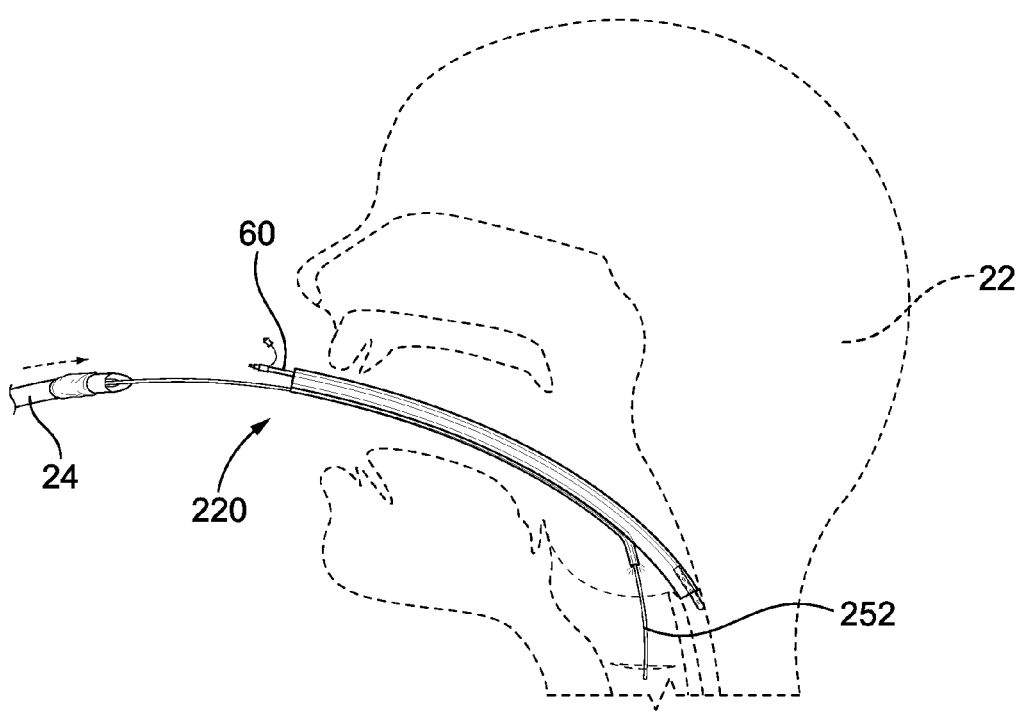
Figure 25C:
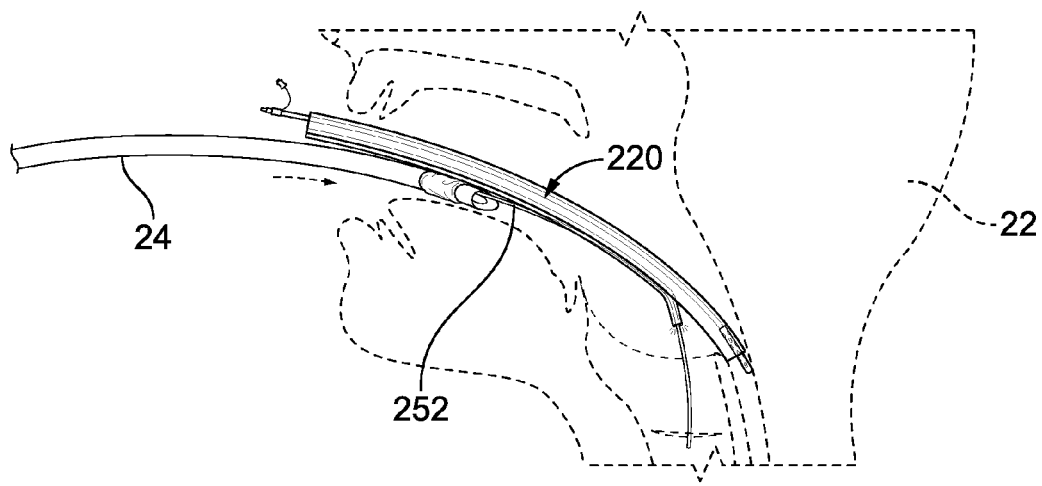
Figure 25D:
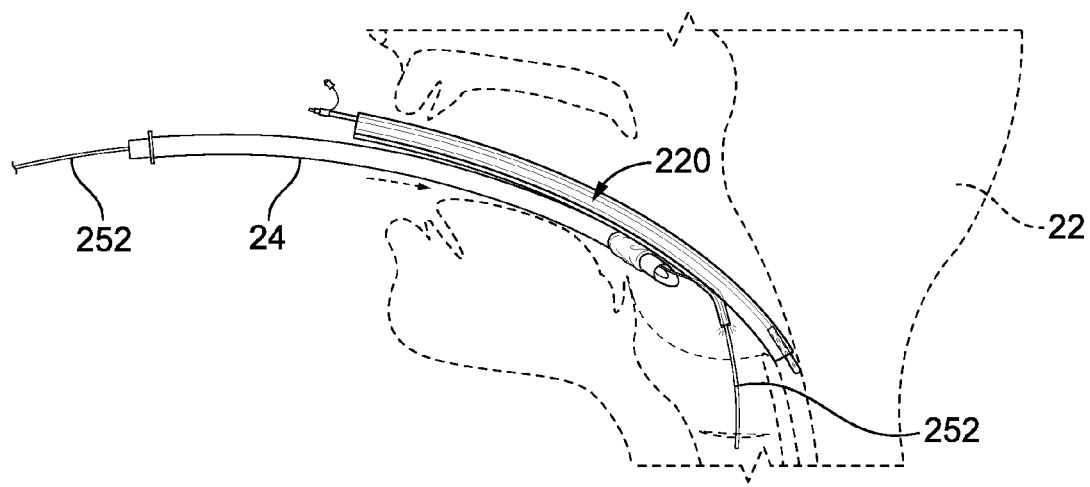
Figure 25E:
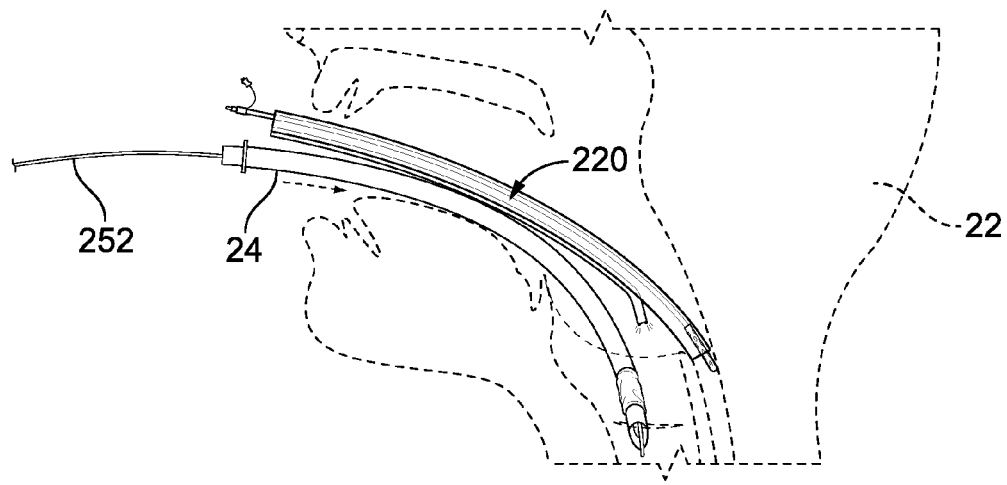

The esophageal tube 226 is formed from an elongated tube wall which as shown in FIG. 23 has first and second portions 230, 232 which are arcuate and which are connected to each other by curved end portions 234, 236. The first and second portions 230, 232 are preferably separate from each other by a distance of mm and the end portions 234, 236 are preferably separated from each other by a distance of 5 mm, however, the esophageal tube 226 may be bigger or smaller. The proximal end of the esophageal tube 226 is open and provides a proximal inlet opening 238. A generally conical end portion 240, see FIG. 24, having an aperture 242 therethrough is provided at the distal end of the tube wall. A central passageway 244 extends through the tube wall and through the conical end portion 240. The aperture 242 is in communication with the central passageway 244. The esophageal tube 226 is curved along its length. The esophageal tube 226 is formed of a relatively stiff but compliant plastics material and is preferably formed by extrusion.

A transmission lumen 68 like that of the first and second embodiments of the medical device 20, 120 is provided and the specifics are not repeated herein. The transmission lumen 68 seats within the central passageway 244 of the esophageal tube 226 and extends from the aperture 242. The transmission lumen 68 may seat freely in the esophageal tube 226, may be attached to the esophageal tube 226 by a friction fit with the aperture 242, or the transmission lumen 68 can be otherwise affixed to the esophageal tube 226.

The intubating tube 228 is formed from a small diameter cylindrical wall 246 having a proximal open inlet (at the end closest to the medical professional), an opposite distal open outlet (at the end furthest away from the medical professional during use of the medical device 220), a central passageway 248 extending therethrough, and a slot 250 which is in fluid communication with the central passageway 248 and extends from the proximal end (at inlet) to the distal end (at outlet) of the intubating tube 228. The intubating tube 228 is curved along its length. The intubating tube 228 has a diameter which is preferably 4 mm, however, the intubating tube 228 may be bigger or smaller. The intubating tube 228 is formed of a relatively stiff but compliant plastics material and is preferably formed by extrusion.

A camera lumen 58/window 60 and camera 66 like that of the first and second embodiments of the medical device 20, 120 are provided and the specifics are not repeated herein.

The intubating tube 228 is affixed, such as by ultrasonic welding, to the esophageal tube 226 along the second wall portion 232. The camera lumen 58 is affixed, such as by ultrasonic welding, to the esophageal tube 226 along the second wall portion 232 and is proximate to the intubating tube 228. The camera 66 and LED lights 62 (or other source of lighting, including a camera with its own built-in lighting) can be incorporated into a single device which is insertable and removeable from the camera lumen 58. The camera 66 is situated to provide the best angle for viewing the tissues of the patient 22 when the medical device 220 is being inserted into the throat of a patient 22. As a result, the intubating tube 228 and the camera lumen 58 are situated side-by-side. The inlets of the esophageal tube 226, the intubating tube 228 and the camera lumen 58 generally align with each other. The outlets do not align with each other; instead, the outlets of the intubating tube 228 and the camera lumen 58 are spaced proximally a predetermined distance from the outlet of the esophageal tube 226. The slot 250 in the intubating tube 228 is opposite to the point of weldment of the intubating tube 228 to the esophageal tube 226 to provide a means for insertion of the endotracheal tube 24 into the patient 22 as described herein.

In use, the medical professional inserts the medical device 220 through the mouth and into the throat of the patient 22. The esophageal tube 226 slides against the hard palate and then against the soft palate and into the pharynx of the patient 22. The medical device 220 will flex to assume a curved shape to conform to the throat of the patient 22. The medical device 220 does not block the airway of the patient 22 so the patient 22 can breathe on his/her own. The generally conical end wall 240 of the esophageal tube 226 enters into the upper end of esophagus 80 such that the transmission lumen 68 is positioned within the esophagus 80 and is located closest to the lungs of the patient 22. The distal outlet of the intubating tube 228 is open to the glottis of the patient 22. During this entire procedure of insertion, the camera 66 provides constant visualization of the tissues during insertion of the medical device 220 into the patient 22. Because the camera 66 provides constant visualization of the tissues during insertion of the medical device 220 into the patient, the medical professional can be assured that the medical device 220 is being properly inserted and positioned in the throat of the patient 22 with limited trauma to the patient 22. Since the camera lumen 58 terminates proximally of the esophageal tube 226 and does not enter into the esophagus 80, the medical professional can see the vocal folds 82 via the camera 66. Since the camera 66 is constantly operating during insertion and through the entire medical procedure, the medical professional can constantly visually confirm that the patient 22 is breathing by the rhythmic opening and closing of the vocal folds 82. The constant visualization of the laryngeal inlet and the vocal folds 82 of the patient 22 can make earlier diagnoses of issues, for example, but not limited to, secretions, tumors, paralyzed vocal folds, apnea, bleeding, and abnormal anatomy, as well as other potentially harmful effects to the patient 22.

The medical device 220 is used to insert the endotracheal tube 24. First, a stylet 252, which is known in the art, is inserted into the intubating tube 228 and the distal end thereof preferably extends past the distal end of the intubating tube. The stylet 252 rides along the portion of the wall 246 of the intubating tube 228 which is proximate to the point of weldment to the esophageal tube 226, and, as such, will not be prone to falling through the slot 250. Thereafter, the distal end of the endotracheal tube 24 is threaded over the proximal end of the stylet 252 (the portion of the stylet 252 which extends from the proximal end of the intubating tube 228). As the endotracheal tube 24 is pushed along the stylet 252, the stylet 252 is pulled upwardly to release it from the intubating tube 228 by the stylet 252 moving through the slot 250. As a result, the endotracheal tube 24 is guided along the proper path by the stylet 252 and the intubating tube 228. Once the stylet 252 is completed released from the intubating tube 228, the endotracheal tube 24 can be further inserted through the vocal folds 82 of the patient 22 under the visualization provided by the camera 66. The medical professional can thus guide the endotracheal tube 24 through the vocal folds 82 and into the trachea, and inflate the cuff of the endotracheal tube 24, under the constant visualization provided by the camera 66. At times, the medical device 220 may be advanced, pulled back, or turned from side to side, to maintain the proper trajectory of the endotracheal tube 24 through the vocal folds 82. This is easily accomplished since there is constant visualization of the tissues via the camera 66.

When the medical device 220 is seated in the throat of the patient 22, the distal end of the transmission lumen 68 is positioned within the esophagus 80 which enables breath and heartbeat sounds to be easily transmitted through the transmission lumen 68 to the medical professional monitoring the patient 22 as described herein.

As a result of the structure of the medical device 220, the intubating tube 228 is located away from the epiglottis 74 of the patient 22 when the medical device 220 is positioned within the patient 22. This minimizes the ability of the epiglottis 74 to block the insertion of the endotracheal tube 24.

Because of the structure of the medical device 220, the patient 22 does not have to be laying on his/her back to effect intubation. The patient 22 can be sitting in a chair, or lying face down.

Like that of the medical devices 20, 120, the video information from the camera 66 and the information from the transmission lumen 68 are transmitted to a microprocessor 82 via appropriate means, such as wires, wireless, Bluetooth, etc., which in turn can transmit the information to another computer, mobile devices, a mobile station and the like, via appropriate means, such as wires, wireless, Bluetooth, etc., and then this information can be accessed by appropriate personnel. This microprocessor 82 can be on-site where the procedure is being performed or can be remote from the procedure site. For example, the information can be supplied to the nurses' station and the nurse on duty will be able to instantly know if the patient 22 is breathing by the visual confirmation that the vocal folds are opening and closing and by hearing breath and heart sounds. The medical professional will be able to interpret the depth of anesthesia by looking at the rhythmic movement of the vocal folds as well as other diagnoses previously mentioned. Other medical personnel can be hundreds of miles away and still be able to monitor, advise, confirm, and diagnose without the patient 22 being in close physical proximity to that medical personnel. Since the camera 66 is constantly operating, medical personnel can tell at any time if the patient 22 is properly ventilated/intubated and is breathing.

Figures 26, 27:
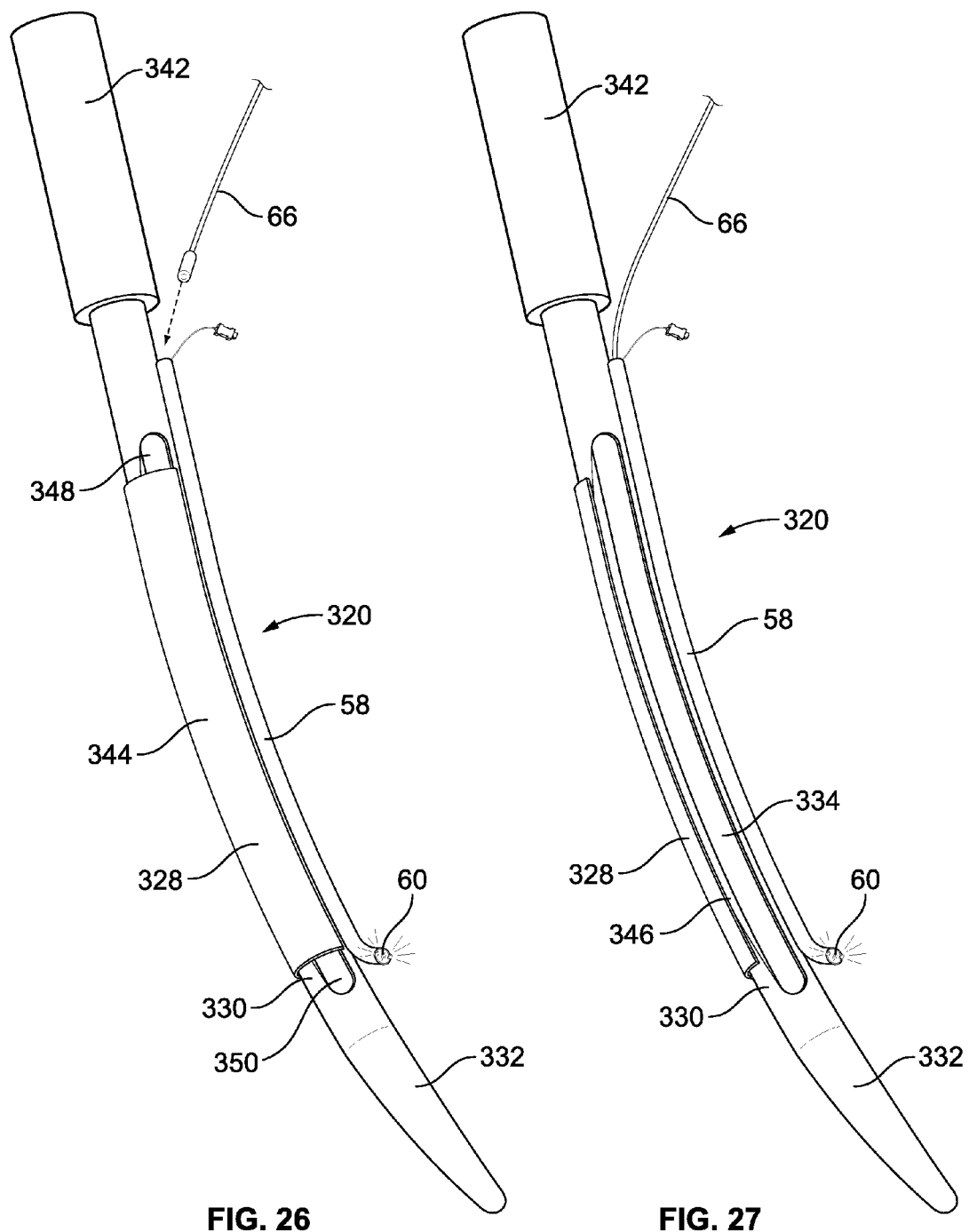
FIGS. 26 and 27 are perspective views of an alternate medical device which incorporates the features of the present invention.

FIGS. 26-318 show an alternate medical device 320 which is inserted into the throat of a patient 22 to determine the status of the internal membranes of the patient 22 and to provide a means for intubating the patient 22 with an endotracheal tube 24. The medical device 320 includes an intubating tube 326 and a sleeve 328 which are connected together. The sleeve 328 is rotatable relative to the intubating tube 326.

Figure 28:
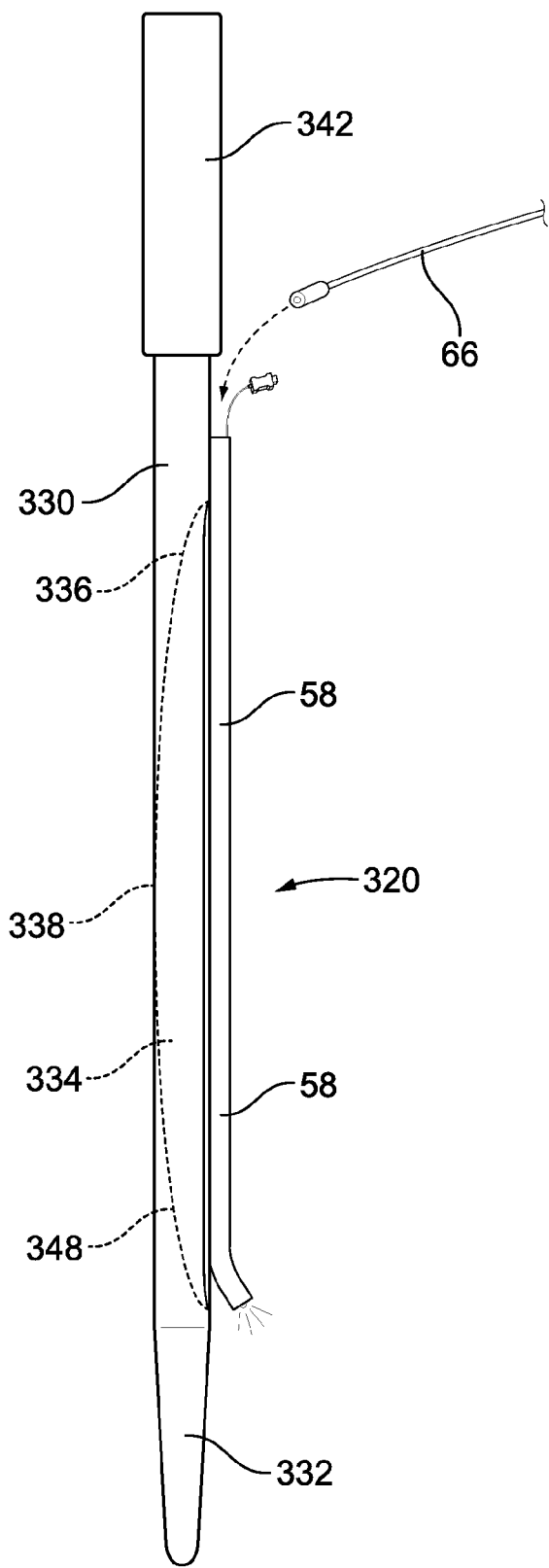
FIG. 28 is a side elevation view of the medical device of FIGS. 26 and 27.
Figures 29, 30:
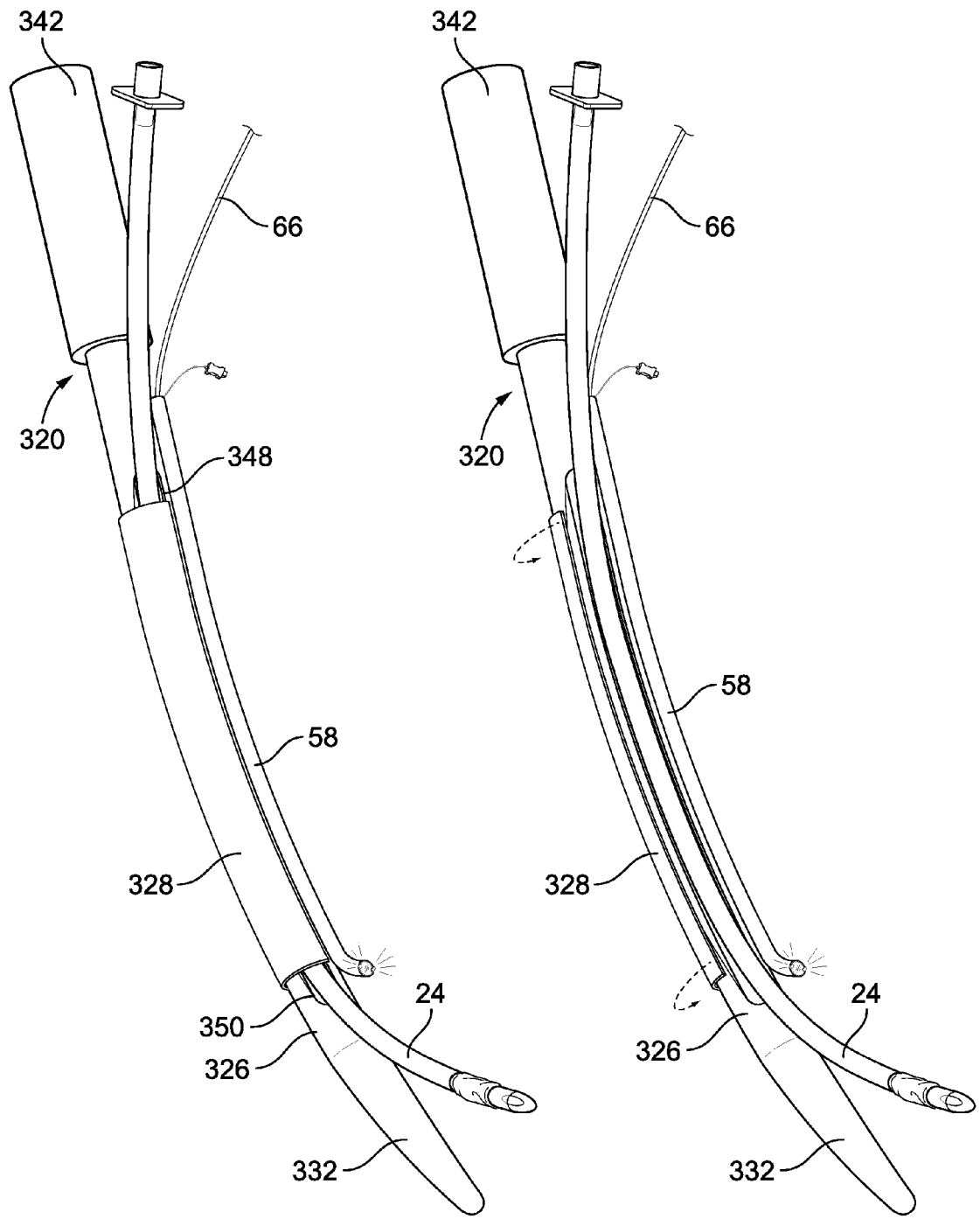
FIGS. 29 and 30 are perspective views of the medical device of FIGS. 26-28, with an endotracheal tube being shown for use therewith.
Figure 31A:
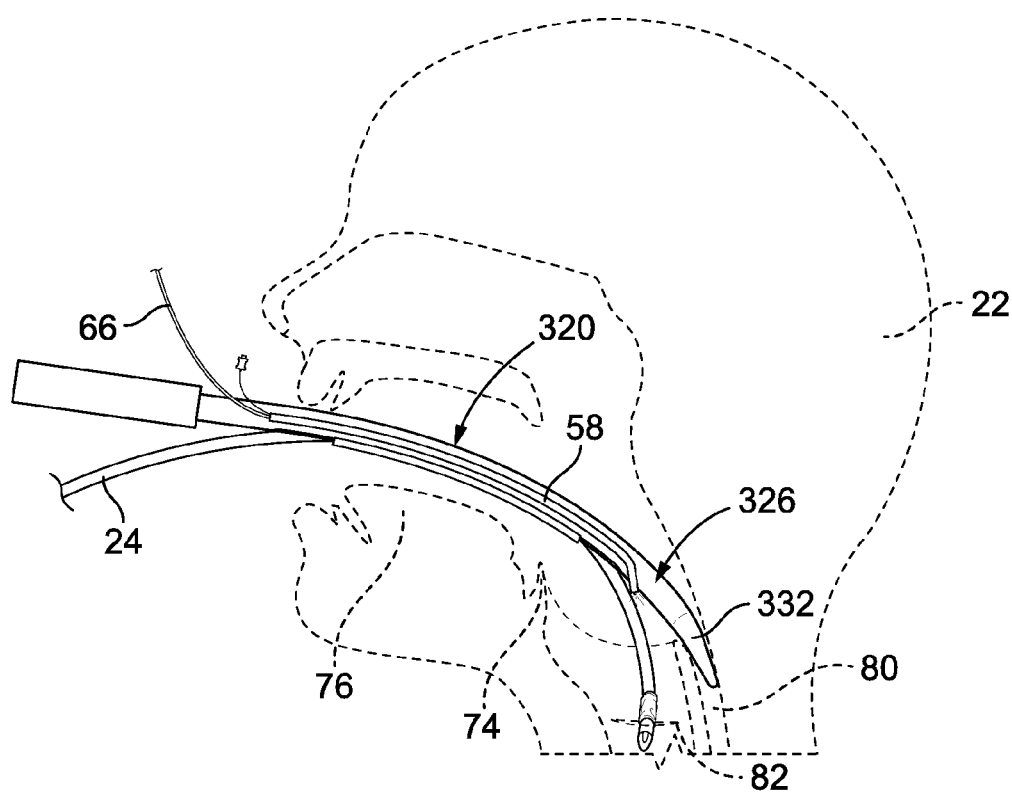
FIGS. 31A and 31B are side elevation views of the medical device of FIGS. 26-28 being inserted into a patient, and being used with an endotracheal tube.
Figure 31B:
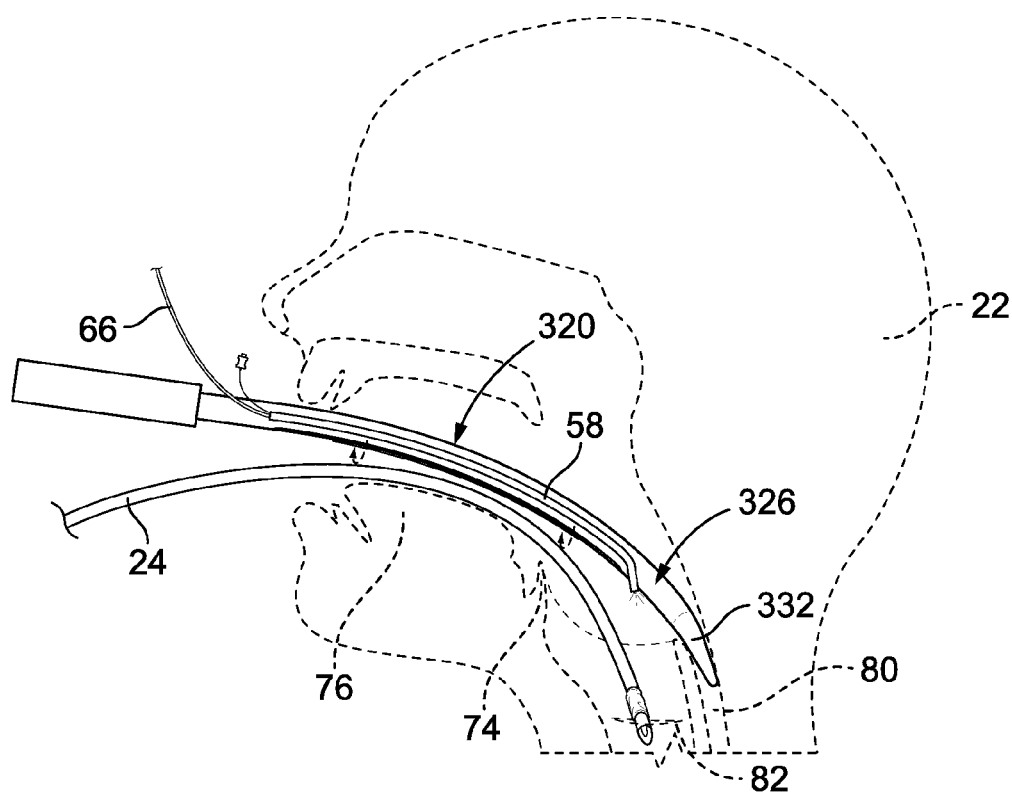

The intubating tube 328 is formed by an elongated cylindrical body 330 which has a generally conical tip 332 at its distal end. The intubating tube 228 is made of a flexible plastic material. The body 330 has an elongated recess 334 therein which generally extends from the proximal end of the body 330 to the distal end of the body 330. The recess 334 is curved along its length such that in cross-section it is generally arcuate as shown in FIG. 28. As a result, a proximal curved ramp surface 336 is formed by the recess 334 and extends from the outer surface of the body 330 proximate to the distal end thereof distally to the apex 338 of the recess 334, and a distal curved ramp surface 340 is formed by the recess 334 and extends from the outer surface of the body 330 proximate to the distal end thereof proximally to the apex 338 of the recess 334. An enlarged cylindrical handle 342 is provided at the distal end of the body 330. The tip 332 has a weight provided therein to make the tip 332 heavier than the remainder of the medical device 320. A camera lumen 58/window 60 and separate camera 66 like that of the previous embodiments of the devices 20, 120, 220 are provided and the specifics are not repeated herein. The camera lumen 58 is preferably positioned beside the recess 334 and the distal end of the camera lumen 58 is proximate to the distal end of the recess 334. The camera lumen 58 is suitably attached to the intubating tube 326 by suitable means, such as ultrasonic welding. Alternatively, the camera lumen 58 can be provided integral with the intubating tube 326.

The sleeve 328 is formed from generally C-shaped wall 344 which defines a slot 346 between the opposite ends of the C-shaped wall 344. The sleeve 328 is made of a flexible plastic material. The sleeve 328 has a length which is less than the length of the recess 334, surrounds a portion of the body 330, and is rotatable relative the body 330 to cover and uncover the majority of the recess 334.

In use, the sleeve 328 is rotated relative to the body 330 such that the recess 334 is partially blocked. The proximal and distal ends of the recess 334 are not blocked by the sleeve 328 such that proximal and distal openings 348, 350 are formed as shown in FIG. 26. The patient 22 then swallows the medical device 320, or the medical professional inserts the medical device 320 through the mouth and into the throat of the patient 22. During this insertion, the recess 334 is proximate to the tongue 76 of the patient 22. The intubating tube 326 slides against the hard palate and then against the soft palate and into the pharynx of the patient 22. The medical device 320 will flex to assume a curved shape to conform to the throat of the patient 22. The medical device 320 does not block the airway of the patient 22 so the patient 22 can breathe on his/her own. The generally conical tip 332 of the intubating tube enters into the upper end of esophagus 80. The proximal opening 348 is positioned exterior to the mouth of the patient 22. The distal opening 350 is open to the glottis of the patient 22. During this entire procedure of insertion, the camera 66 provides constant visualization of the tissues of the patient 22. Because the camera 66 provides constant visualization, the medical professional can be assured that the medical device 320 is being properly inserted and positioned in the throat of the patient 22 with limited trauma to the patient 22. Since the camera lumen 58 terminates proximally of the intubating tube 326 and does not enter into the esophagus 80, the medical professional can see the vocal folds 82 via the camera 66. Since the camera 66 is constantly operating during insertion and through the entire medical procedure, the medical professional can constantly visually confirm that the patient 22 is breathing. The constant visualization of the laryngeal inlet and the vocal folds 82 of the patient 22 can make earlier diagnoses of issues, for example, but not limited to, secretions, tumors, paralyzed vocal folds, apnea, bleeding, and abnormal anatomy, as well as other potentially harmful effects to the patient 22.

The medical device 320 is then used to insert the endotracheal tube 24. The distal end of the endotracheal tube 24 is inserted into the proximal opening 348 and pushed along the length of the recess 334 until the distal end and cuff of the endotracheal tube 24 exit through the distal opening 350 and passes through the vocal folds of the patient 22. The ramp surface 340 at the distal end of the recess 334 aids in properly positioning the endotracheal tube 24 relative to the glottis of the patient 22. The camera 66 is used to determine the positioning of the endotracheal tube 24 and the medical professional can adjust the position of the medical device 320 using this constant visualization provided by the camera 66 to ensure proper entry of the endotracheal tube 24 through the vocal folds 82 and into the trachea of the patient 22. At times, the medical device 320 may be advanced, pulled back, or turned from side to side, to maintain the proper trajectory of the endotracheal tube 24 through the vocal folds 82. This is easily accomplished since there is constant visualization of the tissues via the camera 66. Once the endotracheal tube 24 is properly positioned, the sleeve 328 is rotated relative to the intubating tube 326 and the endotracheal tube 24 is released from the intubating tube 326. The medical device 320 can then be removed from the patient 22 if desired.

A transmission lumen 68 like that of the previous devices 20, 120, 220 may be provided and attached to the intubating tube 326. If provided, when the medical device 320 is seated in the throat of the patient 22, the distal end of the transmission lumen 68 is positioned within the esophagus 80 which enables breath and heartbeat sounds to be easily transmitted along the length of the transmission lumen 68 to the medical professional monitoring the patient 22 as described herein.

As a result of the structure of the medical device 320, the intubating tube 326 is located away from the epiglottis 74 of the patient 22 when the medical device 320 is positioned within the patient 22. This minimizes the ability of the epiglottis 74 to block the insertion of the endotracheal tube 24.

Because of the structure of the medical device 320, the patient 22 does not have to be laying on his/her back to effect intubation. The patient 22 can be sitting in a chair, or lying face down. The medical devices 220, 320 provide a new methodology of intubating the patient 22 by placing the medical device 220, 320 into the esophagus 80 of the patient 22 and working upwardly toward the trachea.

Like that of the previous devices 20, 120, 220, the video information from the camera 66 and the information from the transmission lumen 68 are transmitted to a microprocessor 82 via appropriate means, such as wires, wireless, Bluetooth, etc., which in turn can transmit the information to another computer, mobile devices, a mobile station and the like, via appropriate means, such as wires, wireless, Bluetooth, etc., and then this information can be accessed by appropriate personnel. This microprocessor 82 can be on-site where the procedure is being performed or can be remote from the procedure site. For example, the information can be supplied to the nurses' station and the nurse on duty will be able to instantly know if the patient 22 is breathing by the visual confirmation that the vocal folds are opening and closing and by hearing breath and heart sounds. The medical professional will be able to interpret the depth of anesthesia by looking at the rhythmic movement of the vocal folds 82 as well as other diagnoses previously mentioned. Other medical personnel can be hundreds of miles away and still be able to monitor, advise, confirm, and diagnose without the patient 22 being in close physical proximity to that medical personnel. Since the camera 66 is constantly operating, medical personnel can tell at any time if the patient 22 is properly ventilated/intubated and is breathing.

As an alternative, the endotracheal tube 24 can be seated within the recess 334 prior to insertion of the medical device 320 into the patient 22. The distal portion of the endotracheal tube 24 is preferably trapped between the sleeve 328 and the body 330 when the medical device 320 is first inserted to prevent damage to the cuff of the endotracheal tube 24.

Figures 32, 33:
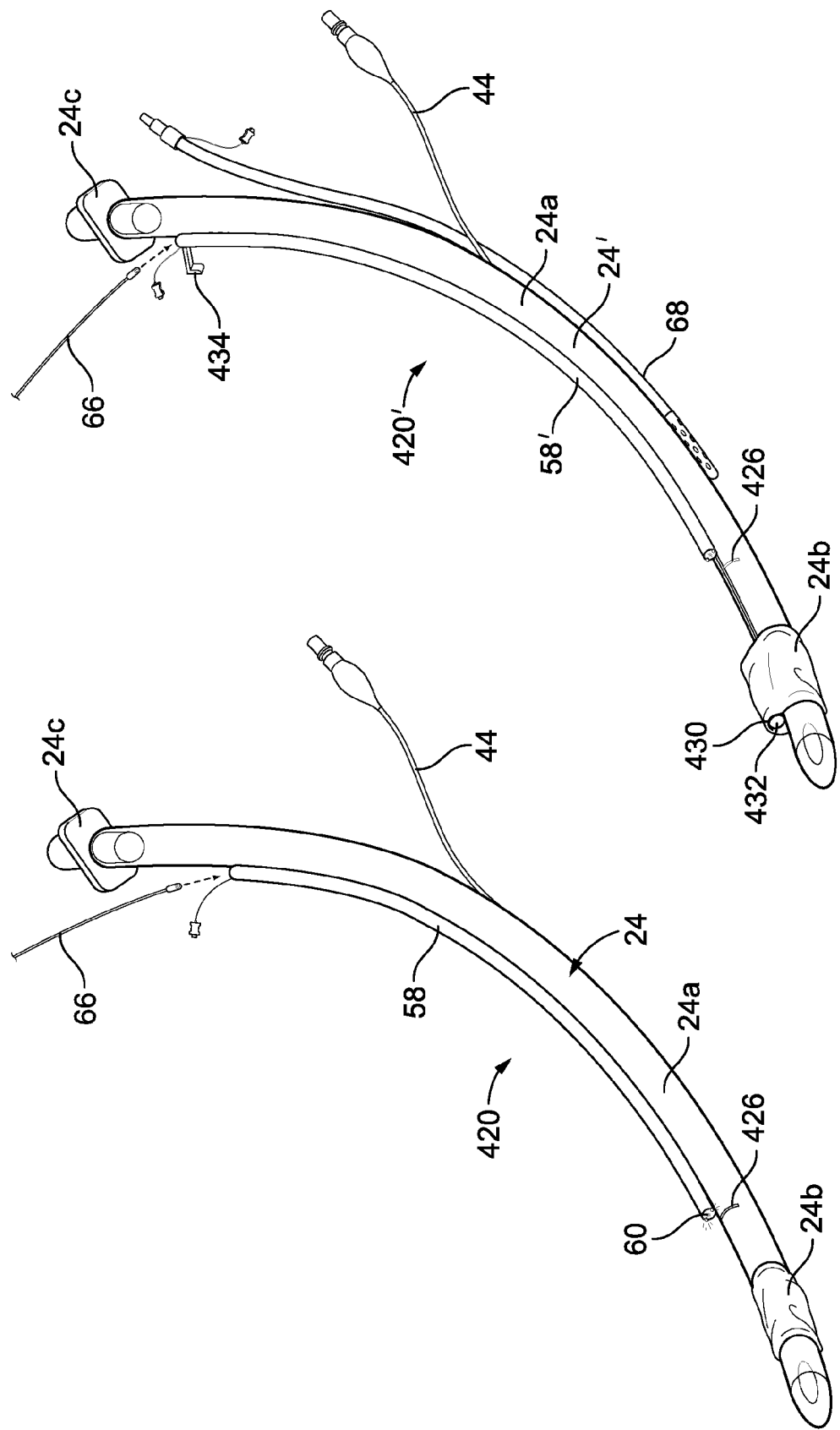
FIG. 32 is a perspective view of another medical device which incorporates the features of the present invention.
FIG. 33 is a perspective view of yet another medical device which incorporates the features of the present invention.

FIG. 32 shows a medical device 420 which includes an endotracheal tube 24 having the camera lumen 58/window 60 affixed thereto. The camera lumen 58/window 60 and separate camera 66 like that of the previous embodiments of the devices 20, 120, 220, 320 are provided and the specifics are not repeated herein.

As is known in the art, the endotracheal tube 24 includes a cylindrical wall 24a formed of a relatively stiff but compliant plastics material and is preferably formed by extrusion which has a central passageway therethrough, a cuff 24b attached proximate to the distal end of the wall 24a which is inflatable via inflation line 44 which is formed by a small-diameter flexible plastic tube. The proximal end of the tube 24a has a connector 24c for connecting the endotracheal tube 24 to a ventilating machine in a known manner. The prior art endotracheal tube 24 is modified in that a mark 426 is provided thereon which is preferably one inch proximal of the cuff 24b.

The camera lumen 58 extends along the length of the wall 24a and the distal end of the camera lumen 58 is proximate to the mark 426. The camera lumen 58 is suitably attached to the wall 24a by suitable means, such as ultrasonic welding. Alternatively, the camera lumen 58 can be provided integral with the wall 24a.

In use, the medical professional inserts the medical device 420 through the mouth and into the throat of the patient 22. The endotracheal tube 24 then passes through the vocal folds and into the trachea of the patient 22. The medical device 420 will flex to assume a curved shape to conform to the throat of the patient 22. If desired, the medical device 420 can be inserted into the patient 22 using the medical device 20, 120. During this entire procedure of insertion, the camera 66 provides constant visualization of the tissues during insertion of the medical device 420 into the patient 22. Because the camera 66 provides constant visualization of the tissues during insertion of the medical device 420 into the patient, the medical professional can be assured that the medical device 420 is being properly inserted and positioned in the throat of the patient 22 with limited trauma to the patient 22. The medical professional can adjust the position of the medical device 420 using this constant visualization provided by the camera 66 to ensure proper entry of the endotracheal tube 24 through the vocal folds and into the trachea of the patient 22. At times, the medical device 420 may be advanced, pulled back, or turned from side to side, to maintain the proper trajectory of the endotracheal tube 24 through the vocal folds. This is easily accomplished since there is constant visualization of the tissues via the camera 66.

The portion of the endotracheal tube 24 distal to the mark 426 passes through the vocal folds, however, the camera lumen 58 does not pass through the vocal folds. As such, the camera 66 is used to continuously visualize the vocal folds and to view the portion of the endotracheal tube 24 which is distal to the vocal folds (when the vocal folds are open) to determine if the endotracheal tube 24 has been properly positioned. Since camera lumen 58 does not pass through the vocal folds, this provides a smaller dimension of material passing through the vocal folds. Since the camera 66 is constantly operating during insertion and through the entire medical procedure, the medical professional can constantly visually confirm that the patient 22 is breathing. The constant visualization of the laryngeal inlet and the vocal folds of the patient 22 can make earlier diagnoses of issues, for example, but not limited to, secretions, tumors, paralyzed vocal folds, apnea, bleeding, and abnormal anatomy, as well as other potentially harmful effects to the patient 22.

A transmission lumen (not shown) like that of the previous devices 20, 120, 220, 320 may be provided and attached to the endotracheal tube 24. If provided, when the medical device 420 is seated in the throat of the patient 22, the distal end of the transmission lumen is positioned proximate to the esophagus which enables breath and heartbeat sounds to be easily transmitted through the transmission lumen to the medical professional monitoring the patient 22.

Figure 34:
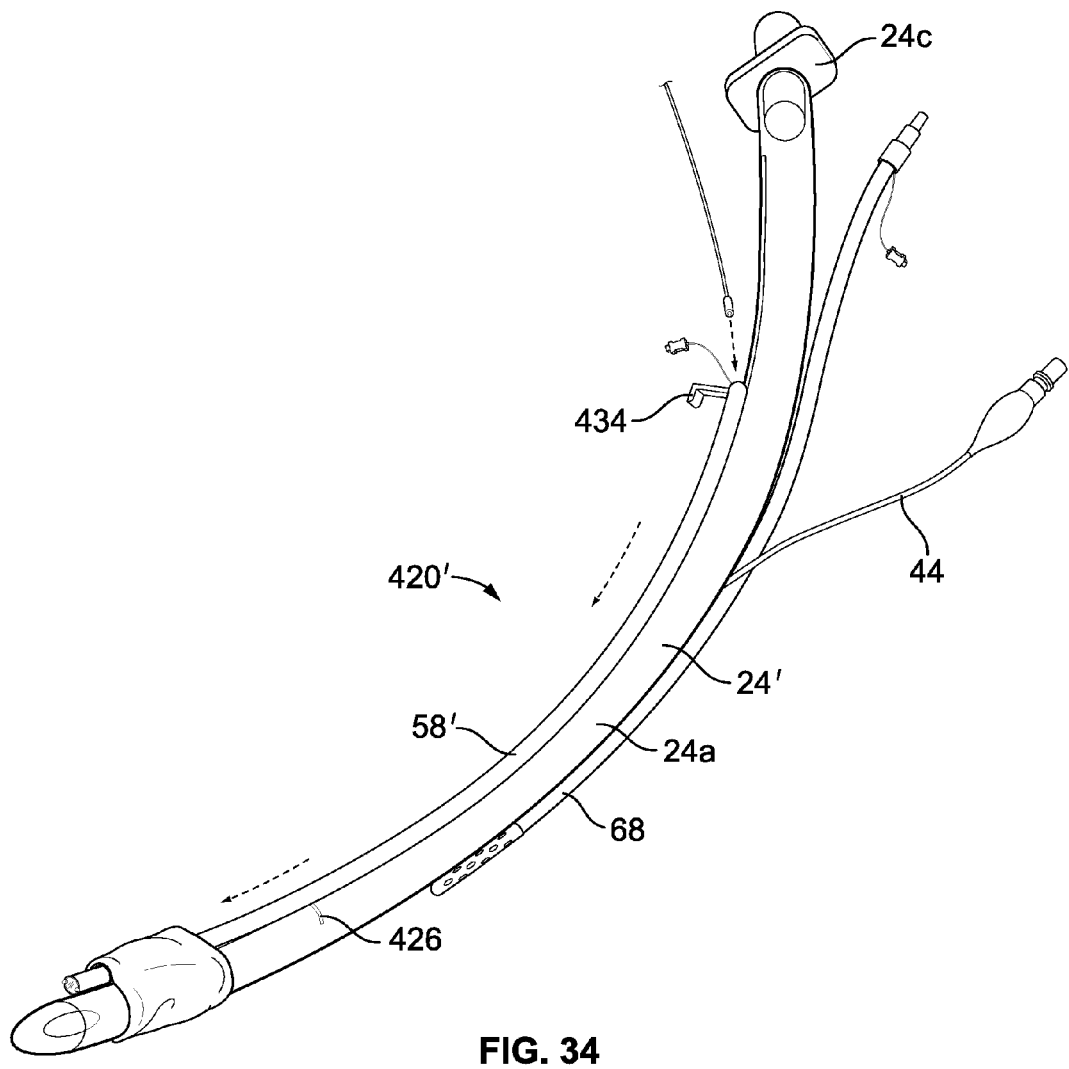
FIG. 34 is a perspective view of the medical device of FIG. 33 in an alternate position.
Figure 35:
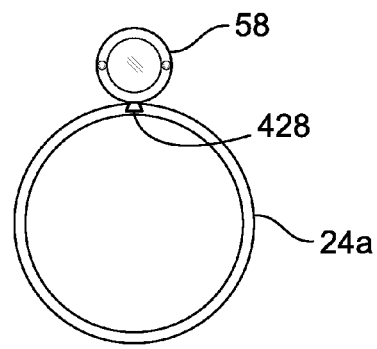
FIG. 35 is a cross-sectional view of the medical device of FIG. 33.

FIGS. 33-35 shown a modified medical device 420' to that shown in FIG. 32 which includes a modified endotracheal tube 24' and a modified camera lumen 58'. The camera lumen 58' is attached to the wall 24a by means which allow the camera lumen 58 to slide relative to the wall 24a. As shown, a dovetail joint 428, formed of a tongue on one of the camera lumen 58 and the wall 24a and of a groove on the other of the camera lumen 58 and the wall 24a, mounts the camera lumen 58 to the wall 24a. A small cylindrical tube 430 is affixed to the wall 24a by suitable means, such as ultrasonic welding, and is provided between the cuff 24b and the wall 24a. A passageway 432 is provided by the small cylindrical tube 430. The distal end of the tube 430 is sealed with a window. The small cylindrical tube 430 is positioned at the end of the structure forming the portion of the dovetail joint 428 on the wall 24b. The camera lumen 58' has a handle 434 attached to its distal end to allow the medial professional to grasp the camera lumen 58' to manipulate the position of the distal end of the camera lumen 58' as described herein.

In use, the medical professional can grasp the handle 434 to slide the camera lumen 58, with the camera 60 mounted therein, along the wall 24a via the inter-engagement of dovetail joint 428 and to slide the distal end of the camera lumen 58/camera 66 through the small cylindrical tube 430. This allows the medical professional to continuously view the tissues of the patient on either side of the vocal folds of the patient 22.

A transmission lumen 68 is affixed to the endotracheal tube 24', preferably to the wall 24a opposite to that where the camera lumen 58' is located. When the medical device 420 is seated in the throat of the patient 22, the distal end of the transmission lumen 68 is positioned proximate to the esophagus which enables breath and heartbeat sounds to be easily transmitted through the transmission lumen 68 to the medical professional monitoring the patient 22.

In the embodiments of the medical device 420, 420', the camera lumen 58, 58'/window 60 could instead be mounted within the endotracheal tube 24, 24', with the mark 426 provided on an interior surface of the endotracheal tube 24, 24'.

Figure 36:
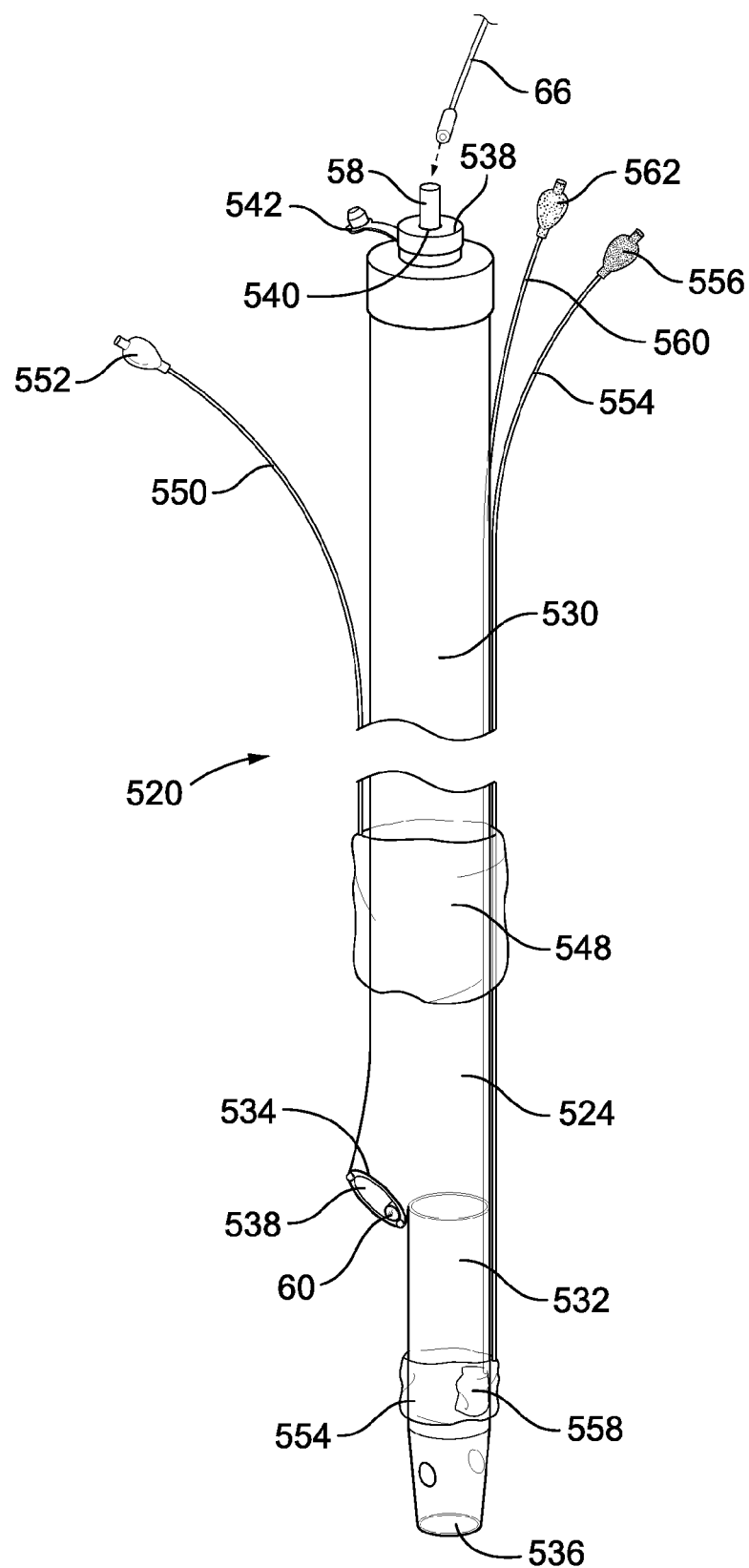
FIG. 36 is a perspective view of another medical device which incorporates the features of the present invention.

FIGS. 36-37B show a medical device 520 formed of a dual branch endotracheal tube 524 which incorporates the sealed camera lumen 58/window 60 and separate camera 66 which can be inserted therein and removed therefrom as described herein. The camera lumen 58/window 60 and separate camera 66 are like that of the previous embodiments of the devices 20, 120, 220, 320, 420, 420' and the specifics are not repeated herein. The dual branch endotracheal tube 524 is used to separate the left and right bronchus 526, 528 from each other for surgical purposes and can be used as a normal endotracheal tube which is normally seated in the trachea of the patient 22. In the prior art, separation of the left and right bronchus 526, 528 from each other is usually accomplished using two lumens which tends to be cumbersome.

The endotracheal tube 524 is formed from a main cylindrical wall 530 having a proximal end (end closest to the medical professional during use) and a distal end (end furthest from the medical professional during use), a first branch cylindrical wall 532 extending from the distal end of the main wall 530, and second branch cylindrical 534 wall extending from the distal end of the main wall 530. The first and second branch walls 532, 534 are smaller in dimension than the main wall 530, but when the dimensions of the branch walls 532, 534 are combined, this dimension is approximately equal to the dimension of the main wall 530. As a result, the endotracheal tube 524 has a single inlet port at its proximal end and first and second outlet ports at its distal end. A central passageway extends through the main wall 530, and branch passageways extend through the branch walls 532, 534, each of which are in communication with the central passageway through the main wall 530. The distal end of the first branch wall 532 has a first port 536 which terminates proximally of the distal end of the second branch wall 534 which forms a second port 538. The second port 538 is angled relative to the first port 536.

The proximal end of the endotracheal tube 524 is closed with a cap 538. The cap 538 has a first aperture 540 therethrough which can be closed with a plug 542 in a known manner, and a second aperture 544 provided through an extension 544 which extends perpendicular to the centerline of the main wall 530. A ventilator is attached to the extension 544 in a known manner to provide positive air pressure to the medical device 520.

An inflatable cuff 548 surrounds the main wall 530 at a position which is spaced from the branch walls 532, 534. An inflation line 550 and its associated pilot 552 is attached to this inflatable cuff 548. An inflatable cuff 554 surrounds the first branch wall 532 at a position which is spaced from the distal port 536. An inflation line 554 and its associated pilot 556 is attached to this inflatable cuff 554. An inflatable cuff 558 (shown in full line in the figures for ease in understanding) is positioned interiorly within the first branch wall 532 at a position which is spaced from the distal port 536. An inflation line 560 and its associated pilot 562 is attached to this interior inflatable cuff 558. The camera lumen 58/window 60 extends through the aperture 540 in the cap 538, through the central passageway in the main wall 530 and into the second branch passageway through the second wall 534 and preferably terminates at, or proximate to, the second port 538. The cap 538 and the lumen 58 can form a frictional fit to prevent the camera lumen 58 from 28 disengaging from the cap 538. The camera 66 is then is inserted into the camera lumen 58.

The medical professional inserts the medical device 520, with all of the cuffs 548, 554, 558 in the deflated condition, through the mouth and into the throat of the patient 22. This insertion can be effected using the medical device 20, 120 as described above. The camera 66 mounted in the medical device 520 provides constant visualization of the tissues of the patient 22 during this insertion.

The medical device 520 can be placed in the patient 22 in one of the three positions. In a first position, the medical device 520 can be placed such that the main wall 530 and the second branch wall 534 are in the trachea of the patient 22 and past the vocal folds 82, and the first branch wall 532 is in the left main stem bronchus 526 of the patient 22, as shown in FIG. 37A. In a second position, the medical device 520 can be placed such that the main wall 530 and the second branch wall 534 are in the trachea of the patient 22 and past the vocal folds 82, and the first branch wall 532 is in the right main stem bronchus of the patient 22 (not shown). In a third position, the medical device 520 can be placed such that the main wall 530 and both branch walls 532, 534 are in the trachea of the patient 22, past the vocal folds 82, but not past the carina 84, as shown in FIG. 37B.

In use, the medical professional inserts the medical device 520 into the patient 22. If desired, the medical device 520 can be inserted into the patient 22 using the medical device 20, 120. The camera 66 is used to continuously visualize the position of the medical device 520 during this insertion. For surgery, the medical device 520 is positioned such that the main wall 530 and the second branch wall 534 seat in the trachea of the patient 22 and the first branch wall 532 seats into one of the bronchus of the patient 22 (left as shown in the drawings). Since the camera 66 is positioned in the trachea of the patient 22, the carina 84 of the patient 22 is always within view and the medical professional will know that the first branch wall 532 is positioned within the bronchus of the patient 22. Once properly positioned, the external cuffs 548, 554 are inflated to hold the medical device 520 in place. Cuff 548 engages with the trachea of the patient 22, and cuff 554 engages with the bronchus of the patient 22. The camera 66 provides visual confirmation that the cuff 554 has been inflated in the bronchus. When the surgeon wants to operate on the lung, the medical professional disconnects the ventilator from extension 544 to allow both lungs to deflate. Thereafter, the internal cuff 558 is inflated to block airflow through the branch wall to the bronchus in which the first branch wall 532 is seated. Thereafter, ventilation is resumed such that the lung which will not be operated upon is functioning. Once the medical procedure is completed, all of the cuffs 548, 554, 558 are deflated and the medical device 520 is pulled proximally to remove the second branch wall 532 from the bronchus. As a result, the main wall 530 and both branch walls 532, 534 are seated within the trachea. The camera 66 again provides visual confirmation of the position of the medical device 520 in the trachea as the carina 84 can be seen.

Once the medical device 520 is positioned completely in the trachea, the pilots 556, 560 to the inflation lines 554, 560 to the distal cuffs 554, 558 are cut as shown in FIG. 37B to prevent their inflation. The main cuff 548 is then re-inflated and the medical device 520 functions as a normal endotracheal tube. This medical device 520 can be modified to include the camera lumen shown in FIGS. 32-35 to allow the medical professional to view the tissues above or below the vocal folds 82.

This structure presents a distinct advantage over prior art double lumen endotracheal tubes. Prior art double lumen endotracheal tubes are much wider than the present medical device 520, which may cause undue harm to the patient.

Figures 38, 39A, 39B, 39C:
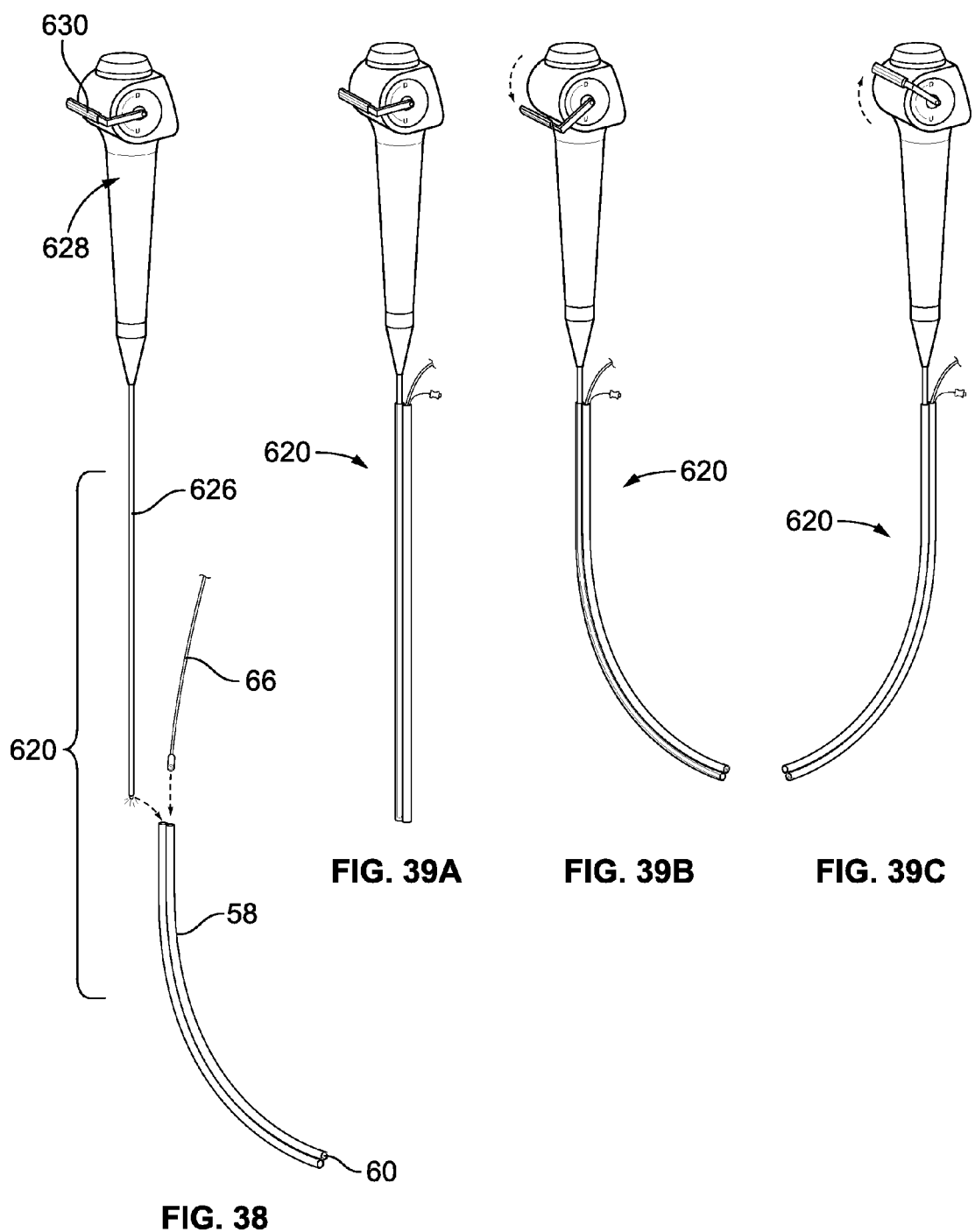

FIGS. 38-39C show a medical device 620 which is a modified bronchoscope which has the camera lumen 58/window 60 and separate camera 66. The camera lumen 58/window 60 and separate camera 66 are like that of the previous embodiments of the devices 20, 120, 220, 320 and the specifics are not repeated herein.

In the prior art, bronchoscopes use a fiber optic line, the position of which can be manipulated by the mechanism at the proximal end of the fiber optic line. As is known in the prior art, the handle on the mechanism can be toggled to cause the fiber optic line to curved either to the left or to the right. Prior art bronchoscopes are expensive because of the built-in fiber optics and if this fiber optic line is compromised, the entire bronchoscope must be replaced.

The medical device 620 replaces the fiber optic line of the prior art bronchoscope, with an elongated plastic line 626 which is flexible, yet maintains its rigidity. The position of the plastic line 626 is manipulated by the same mechanism 628 which is known in the prior art bronchoscope to cause the plastic line 628 to curve to the left or to the right (shown in FIGS. 39B and 39C) by toggling the handle 630.

The medical device 620 has the camera lumen 58/window 60 affixed to the elongated plastic line 626 by suitable means, such as ultrasonic welding, such that the plastic line 626 and the camera lumen 58 are side-by-side. The distal ends of the plastic line 626 and the camera lumen 58 preferably terminate at the same point. As is described herein with respect to the other embodiments, the camera 66 is removably placed in this sealed camera lumen 58.

In use, the medical professional inserts the plastic line 626/camera lumen 58 with the camera 66 mounted therein into the patient 22 and uses it like a prior art bronchoscope. The camera 66 provides constant visualization of the tissues of the patient 22.

The medical device 620 can be used in place of the camera lumen 58 in the medical devices 420, 420', 520 disclosed herein. The medical device 620 can be used to place the medical devices 420, 420', 520 in the patient 22.

Figure 40:
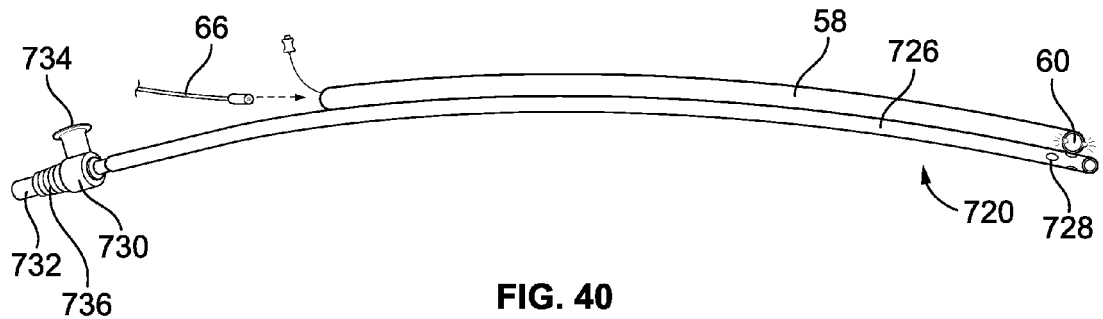
FIG. 40 shows a perspective view of yet another medical device which incorporates the features of the present invention.

FIG. 40 shows a medical device 720 which is used to provide suction to a cavity of the patient 22, such as the lungs, the chest cavity, etc. to drain fluids/air from the cavity. The medical device 720 includes a cylindrical suction tube 726 which is known in the art which is attached to the camera lumen 58/window 60 and separate camera 66. The camera lumen 58/window 60 and separate camera 66 are like that of the previous embodiments of the devices 20, 120, 220, 320, 420, 420', 520, 620 and the specifics are not repeated herein.

The suction tube 726 has a proximal open inlet (at the end closest to the medical professional), an opposite distal outlet (at the end furthest away from the medical professional during use) and a central passageway extending therethrough. The suction tube 726 is curved along its length. The distal end of the suction tube 726 has a series of perforations 728. The suction tube 726 is formed of a relatively stiff but compliant plastics material and is preferably formed by extrusion. The proximal end of the suction tube 726 has a connector 730 attached thereto as is known in the art. The connector 730 has two ports 732, 734 which are perpendicular to each other. As is known in the art, port 732 is attached to a suction device (not shown); the ribs 736 on the port 732 help retain the suction device thereon. When the suction device is turned on, air will be entrained from the open port 734. The medical professional places his/her thumb or otherwise blocks the port 734 to cause the suction tube 726 to suck fluids from the distal end through the perforations 728.

The camera lumen 58 is affixed, such as by ultrasonic welding, to the suction tube 726, such that the suction tube 726 and the camera lumen 58 are side-by-side. The distal ends of the suction tube 726 and the camera lumen 58 preferably terminate at the same point. As is described herein with respect to the other embodiments, the camera 66 is removably placed in this sealed camera lumen 58.

In use, the medical professional inserts the medical device 720 through the endotracheal tube 24, through a drain line (not shown) or directly into the patient's cavity. The camera 66 provides constant visualization of the tissues during insertion and use of the medical device 720 into the patient 22 and the medical professional can be assured that the medical device 720 is being properly positioned in the patient 22 with limited trauma to the patient 22. The constant visualization of the tissues of the patient 22 can make earlier diagnoses of issues, for example, but not limited to, secretions, tumors, paralyzed vocal folds, apnea, bleeding, and abnormal anatomy, as well as other potentially harmful effects to the patient 22.

The medical device 720 can be used in combination with many of the other medical devices disclosed herein.

Figure 41:
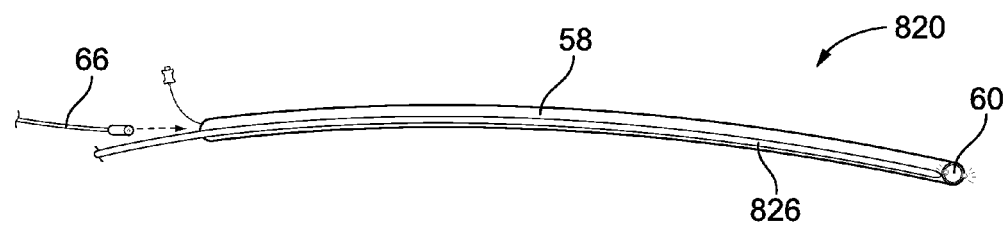
FIG. 41 shows a perspective view of yet another medical device which incorporates the features of the present invention.

FIG. 41 shows a medical device 820 which provides a stylet 826 which is known in the art which is attached to the camera lumen 58/window 60 and separate camera 66. The camera lumen 58/window 60 and separate camera 66 are like that of the previous embodiments of the devices 20, 120, 220, 320, 420, 420', 520, 620, 720 and the specifics are not repeated herein.

The camera lumen 58 is attached to the stylet 826 by suitable means, such as ultrasonic welding or a dovetail joint between the camera lumen 58 and the stylet 82, such that the stylet 826 and the camera lumen 58 are side-by-side. The distal ends of the stylet 826 and the camera 32 lumen 58 preferably terminate at the same point. As is described herein with respect to the other embodiments, the camera 66 is removably placed in this sealed camera lumen 58 to continuously visualize the path the stylet 826 takes during insertion into the patient 22.

Figure 42:
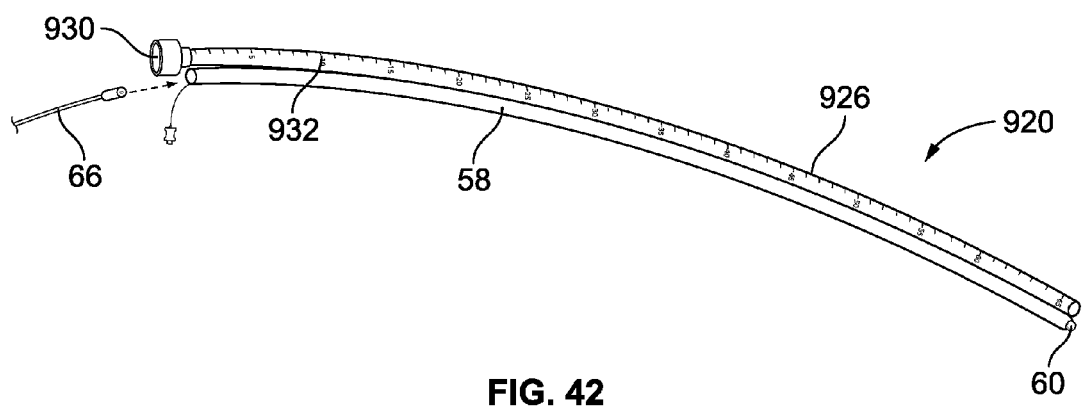
FIG. 42 shows a perspective view of another medical device which incorporates the features of the present invention.

FIG. 42 shows a medical device 920 which provides a tube changer 926 which is known in the art which is attached to the camera lumen 58/window 60 and separate camera 66. The camera lumen 58/window 60 and separate camera 66 are like that of the previous embodiments of the devices 20, 120, 220, 320, 420, 420', 520, 620, 720, 820 and the specifics are not repeated herein.

As is known in the art, tube changers are used to change one endotracheal tube for another endotracheal tube. The tube changer 926 is formed of an elongated, relatively stiff but compliant plastics material and is preferably formed by extrusion. The tube changer 926 has a proximal end, a distal end and a central passageway therethrough. The proximal end of the changer 926 is capped with a connector 930 that can be connected to a ventilator.

The camera lumen 58 is attached to the tube changer 926 by suitable means, such as ultrasonic welding or a dovetail joint between the camera lumen 58 and the tube changer 926, such that the tube changer 926 and the camera lumen 58 are side-by-side. The distal ends of the tube changer 926 and the camera lumen 58 preferably terminate at the same point. As is described herein with respect to the other embodiments, the camera 66 is removably placed in this sealed camera lumen 58 to continuously visualize the path the tube changer 926 takes during insertion into the patient 22.

In use, the medical professional feeds the medical device 920 through the endotracheal tube that is to be removed until the distal end of the medical device 920 is positioned proximate to the carina 84 of the patient 22. The medical professional can see the distal end of the endotracheal tube as the camera 66 passes thereby and can see the carina 84. The medical professional uses the camera 66 to constantly visualize the tissues and to determine when the distal end of the medical device 920 is proximate to the carina 84. The connector 930 is removed from the medical device 920 and the endotracheal tube is then removed from the patient 22. If necessary, the patient 22 can be ventilated through the medical device 920 by attaching the connector 930 to the tube changer 926 and attaching a ventilator to the connector 930. In order to insert the new endotracheal tube, the connector 930 is removed from the tube changer 926. The new endotracheal tube (which may be one of the endotracheal tube shown in FIGS. 32-37B) is fed over the medical device 920 and into the trachea of the patient 22. The medical device 920 is then pulled proximally. Once the distal end of the new endotracheal tube is sighted using the camera 66, the medical professional must also be able to see the carina 84 to ensure that the new endotracheal tube was not inserted too far into the trachea (if the endotracheal tube is positioned too deeply, the endotracheal tube can abut the carina 84, or can be positioned in one of the bronchus of the patient 22). The new endotracheal tube can be repositioned at this time if necessary using the camera 66 for the proper positioning. Once the new endotracheal tube is properly positioned, the medical device 920 is removed from the new endotracheal tube. The camera 66 can be removed from the camera lumen 58 and placed into the new endotracheal tube as discussed herein.

The tube changer 926 may have graduation marks 932 thereon between the ends which may be used to double check the position of the new endotracheal tube in accordance with the known Seldinger technique. Since the camera 66 provides visual confirmation of the correct placement of the endotracheal tube, the graduations marks 932 are not necessary.

Figure 43:
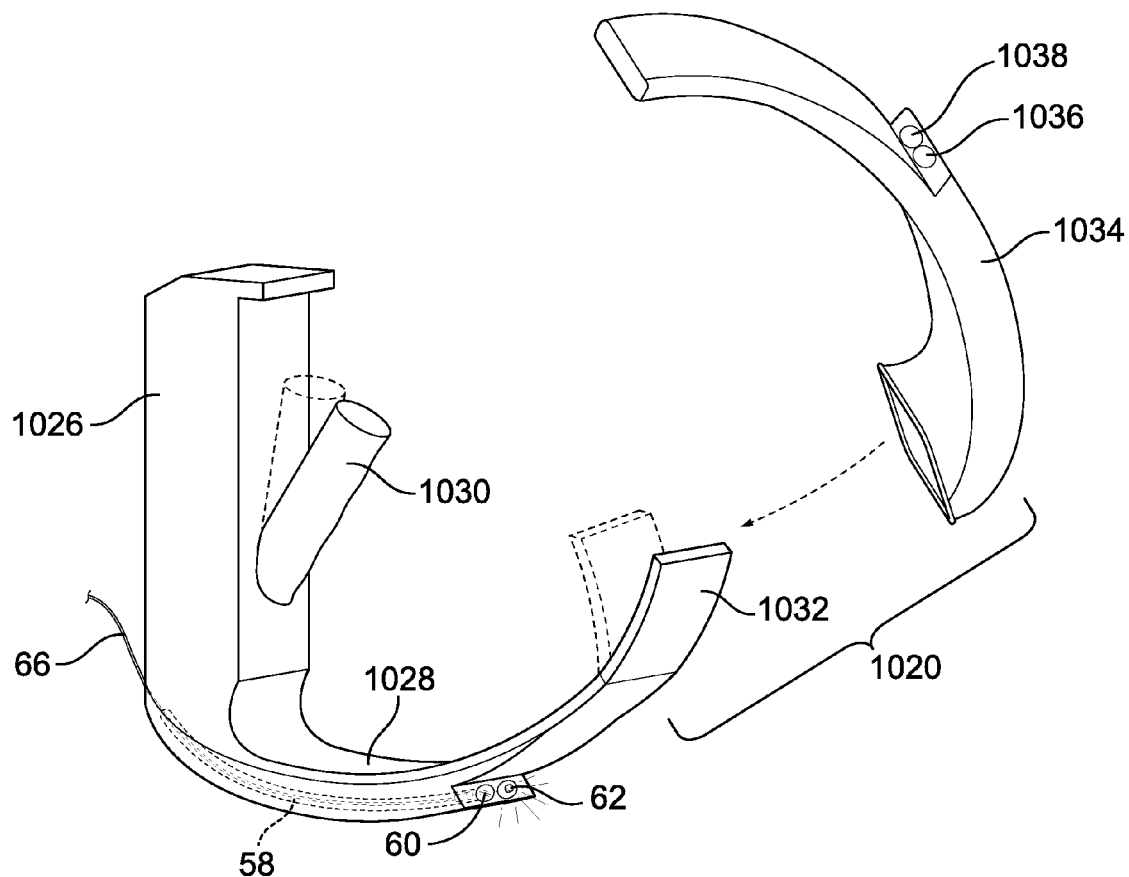
FIGS. 43 and 44 show perspective views of yet a further medical device which incorporates the features of the present invention.
Figure 44:
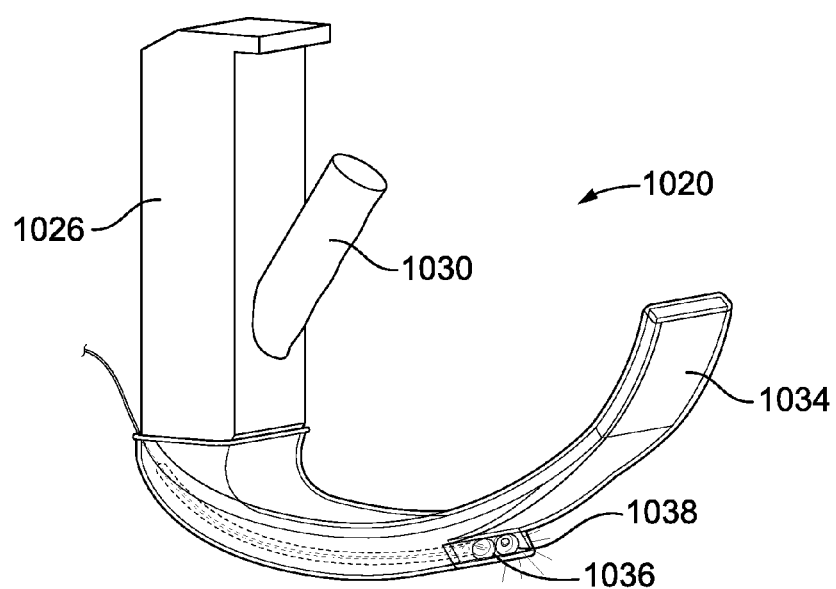

FIGS. 43 and 44 show a medical device 1020 which is used to manipulate the position of the epiglottis 74 of the patient 22 for intubation purposes which is similar to a medical device commonly sold under the trademark GLIDESCOPE® which is owned by Verathon Medical (Canada) ULC. The medical device 1020 has a handle 1026 and curved body 1028 extending from one end of the handle 1026. The handle 1026 has a finger grip handle 1030 extending therefrom at a forty-five degree angle. The finger grip handle 1030 can be flexed relative to the handle 1026. A tip 1032 is provided at the opposite end of the body 1028 and can be flexed relative to the body 1028. A mechanism (not shown), which is known in the art, is embedded in the medical device 1020 and connects the finger grip handle 1030 to the tip 1032. When the medical device 1020 is held by a medical professional, the handle 1026 seats in the palm of the medical professional and the fingers of the medical professional wrap around the finger grip handle 1030. When the medical professional squeezes his/her fingers, the finger grip handle 1030 moves toward the handle 1026 and this causes the internal mechanism to move the tip 1032 toward the handle 1026. This is known in the prior art.

The prior art medical device 1020 has been modified in two respects. First, integral camera lumen 58/window 60 and LED lights 62 are provided. The integral camera lumen 58 extends along a section of the body 1028. The window 60 is sealed to the camera lumen 58 to prevent the entry of fluids and other matter into the camera lumen 58. This camera lumen 58 terminates at approximately the midpoint of the body 1028. Second, a disposable sleeve 1034 which conforms to the shape of the tip 1032 and body 1028 is provided. The sleeve 1034 is formed of a thin plastic material. The sleeve 1034 has apertures 1036, 1038 therethrough to remove any obstruction from the view of the camera 66 and to allow the lights 62 to shine therethrough in an unobstructed manner. The lights 62 can be incorporated into the sleeve 1034 instead of the body 1028.

In use, the camera 66 is inserted into the camera lumen 58 and the sleeve 1034 covers the tip 1032 and body 1028. The apertures 1036, 1038 in the sleeve 1034 align the window 60 and the lights 62. The medical professional inserts the medical device 1020 into the mouth of the patient 22 and the tip 1032 enters into the vallecula 110. The body 1028 generally mirrors the shape of the patient's tongue 76. The sleeve 1034 prevents the patient's tissues and secretions from contacting the remainder of the medical device 1020. The handle 1026 seats in the palm of the medical professional and the fingers of the medical professional wrap around the finger grip handle 1030. The entry of the tip 1032 into the mouth of the patient 22 is continuously visualized by the camera 66 in the sealed camera lumen 58. Once the tip 1032 is properly positioned in the vallecula 110, the medical professional's fingers are squeezed and the finger grip handle 1030 moves toward the handle 1026. This causes the internal mechanism in the body 1028 to move the tip 1032 toward the handle 1026. The tip 1032 engages the patient's tongue 76 and pulls the tongue 76 proximally toward the outside of the mouth of the patient 22. As a result, the epiglottis 74 is also pulled proximally to further open the airway of the patient 22.

With the epiglottis 74 pulled proximally, the medical professional inserts the medical device 20, 120 or the medical device 420, 420', 520 in the patient's throat as described herein. The camera 66 can be removed from the medical device 1020 and inserted into the medical device 20, 120 or medical device 420, 420', 520.

In all of the devices 20, 120, 220, 320, 420, 420', 520, 620, 720, 820, 920, 1020 described herein, the same camera 66 can be easily slid into and removed from all of the sealed camera lumens 58. As a result, the camera 66, which is an expensive component, can be used in multiple different devices such as those as shown (or other devices which have such a sealed camera lumen) by removing it from one device and inserting it into another device. Since the camera lumen 58 is sealed, it is not necessary to sterilize the camera 66 between uses as the camera 66 does not come into contact with the tissues and/or secretions of the patient 22.

While specific lumens (camera lumen, transmission lumen) are shown and described with respect to each of the embodiments, it is to be understood that other lumens can also be provided each of the embodiments. Such other lumens could be used for insertion of other tools into the patient 22, for the providing oxygen to the patient 22, for suctioning fluids from the patient 22 and the like.

A transmission lumen 68 can be used in any of the devices 20, 120, 220, 320, 420, 420', 520, 620, 720, 820, 920, 1020. If such a transmission lumen 68 is provided, a speaker (not shown) can included to audibilize the breath and heart sounds from the patient 22 transmitted from the transmission lumen 68. The sound from the transmission lumen 68 can be magnified and externalized to the devices. The speaker can be disseminated electronically. The speaker can be provided in any one of the lumens or tubes, or suitably connected to the lumens or tubes.

Figures 45, 46:
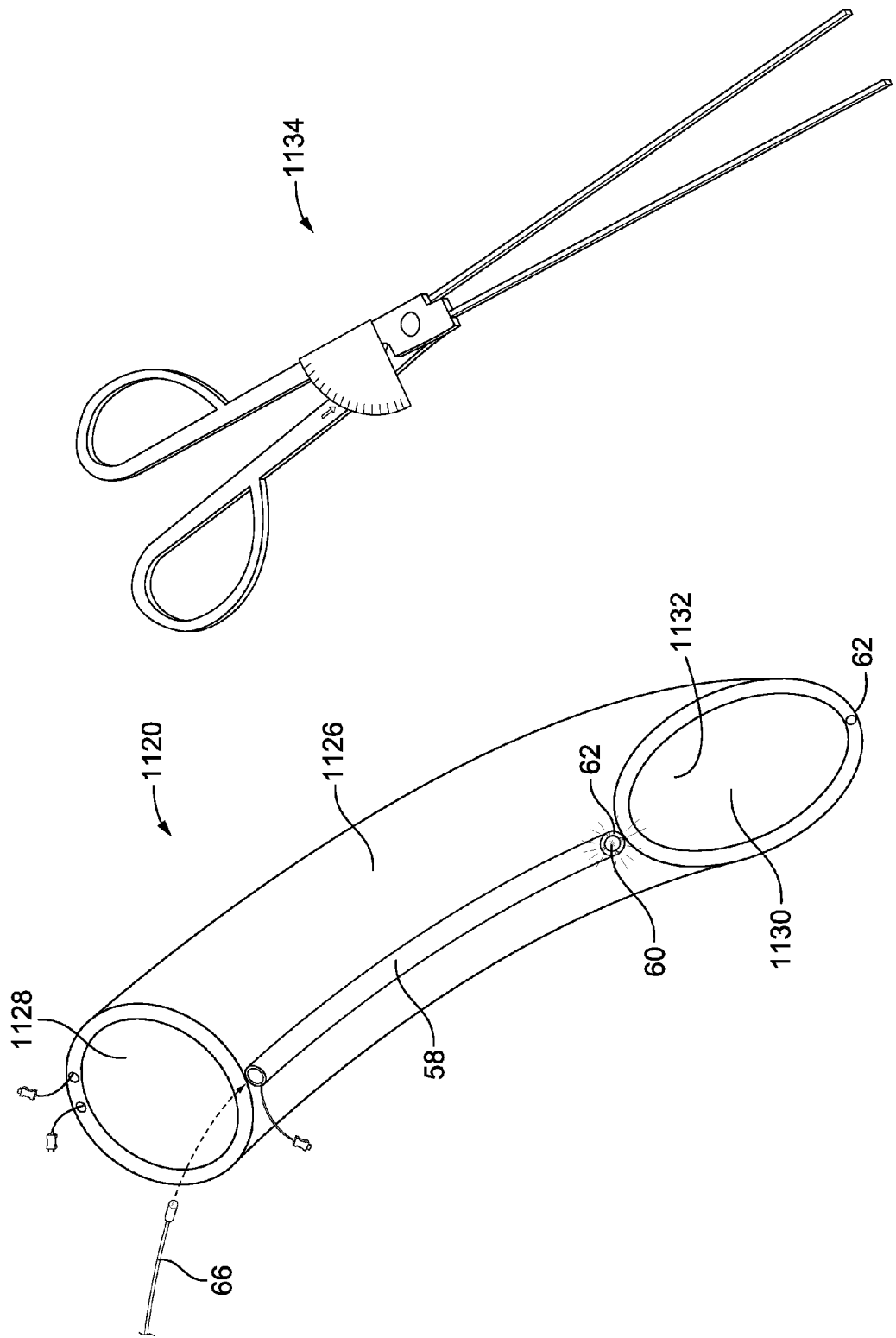
FIG. 45 shows a perspective view of another medical device which incorporates the features of the present invention.
FIG. 46 shows a perspective view of a tool which can be used with the medical device of FIG. 45.

FIGS. 45 and 46 show a medical device 1120 which is allows a medical professional, such as an obstetrician/gynecologist (OB/GYN), to easy view the cervix of a patient to determine the amount of dilation of the cervix. The medical device 1120 includes a cylindrical tube 1126 which has the camera lumen 58/window 60 attached thereto. The separate camera 66 is insertable and removable from the camera lumen 58. The camera lumen 58/window 60 and separate camera 66 are like that of the previous devices 20, 120, 220, 320, 420, 420', 520, 620, 720, 820, and the specifics are not repeated herein.

The tube 1126 has a proximal open inlet 1128 (at the end closest to the medical professional), an opposite distal outlet 1130 (at the end furthest away from the medical professional during use) and a central passageway 1132 extending therethrough. The tube 1126 may be curved along its length, or it may be straight. The tube 1126 is formed of a relatively stiff but compliant plastics material and is preferably formed by extrusion.

The camera lumen 58 is affixed, such as by ultrasonic welding, to the tube 1126, such that the tube 1126 and the camera lumen 58 are side-by-side. The camera lumen 58 can be on the external surface or external surface of the tube 1126. The proximal and distal ends of the tube 1126 and the camera lumen 58 preferably are at the same points. As is described herein with respect to the other embodiments, the camera 66 is removably placed in this sealed camera lumen 58. As in the previous devices, an LED light 62 can be provided at the distal end 1130 of the tube 1132 or camera lumen 58 to illuminate the tissues, or in the camera 66 itself.

In use, the medical professional inserts the medical device 1120 into the patient's vagina such that the cervix can be seen. The camera 66 provides constant visualization of the cervix and tissues during insertion and use of the medical device 1120 in the patient and the medical professional can be assured that the medical device 1120 is being properly positioned in the patient with limited trauma to the patient. The constant visualization of the tissues of the patient can make earlier diagnoses of issues, for example, but not limited to, secretions, tumors, bleeding, and abnormal anatomy, as well as other potentially harmful effects to the patient.

After the medical device 1120 is positioned, the medical professional can use a tool, such as the tool 1134 shown in FIG. 46, to measure the amount of dilation of the cervix. The medical device 1120 remains in place during the labor. The camera 66 provides a constant stream of information to the medical professional regarding the amount of dilation of the patient.

In any of the devices 20, 120, 220, 320, 420, 420', 520, 620, 720, 820, 920, 1020, 1120, the video information from the camera 66 and/or the information from the transmission lumen 68 are transmitted to a microprocessor 82, FIG. 11, via appropriate means, such as wires, wireless, Bluetooth, etc., which in turn can transmit the information to another computer, mobile devices, a mobile station and the like, via appropriate means, such as wires, wireless, Bluetooth, etc., and then this information can be accessed by appropriate personnel. This microprocessor 82 can be on-site where the procedure is being performed or can be remote from the procedure site. For example, the information can be supplied to the nurses' station and the nurse on duty will be able to instantly know if the patient 22 is breathing by the visual confirmation that the vocal folds are opening and closing and by hearing breath and heart sounds. The medical professional will be able to interpret the depth of anesthesia by looking at the rhythmic movement of the vocal folds as well as other diagnoses previously mentioned. Other medical personnel can be hundreds of miles away and still be able to monitor, advise, confirm, and diagnose without the patient 22 being in close physical proximity to that medical personnel. Since the camera 66 is constantly operating, medical personnel can tell at any time if the patient 22 is properly ventilated/intubated and is breathing.

In any of the devices 20, 120, 220, 320, 420, 420', 520, 620, 720, 820, 920, 1020, 1120, the LED light 62 can be provided at the distal end of the device 20, 120, 220, 320, 420, 420', 520, 620, 720, 820, 920, 1020, 1120, in camera lumen 58, or in the camera 66 itself to illuminate the tissues. In addition, multiple LED lights 62 can be provided in each of the 20, 120, 220, 320, 420, 420', 520, 620, 720, 820, 920, 1020, 1120 and can be located on different parts of the devices 20, 120, 220, 320, 420, 420', 520, 620, 720, 820, 920, 1020, 1120.

While preferred embodiments of the present invention are shown and described, it is envisioned that those skilled in the art may devise various modifications of the present invention without departing from the spirit and scope of the appended claims.

What is claimed is:

1. An assembly comprising: a medical device for insertion into a cavity of a patient, said medical device comprising: a wall having a proximal end and a distal end, and a passageway extending between said proximal and distal ends; a camera lumen having a sealed window at one end thereof, said camera lumen attached externally to said wall of said medical device; and a separate camera inserted into said camera lumen, said camera being removable from said camera lumen, wherein the camera provides continuous visualization of patient's tissues; wherein the medical device further comprises an inflatable cuff attached proximate to the distal end of said wall; and a small cylindrical tube affixed to said wall and provided between said inflatable cuff and said wall, said small cylindrical tube having a passageway therethrough, said camera lumen is slidably connected to said wall and can be slid into and out of said small cylindrical tube proximally and distally to the inflatable cuff to provide visualization proximally and distally of the inflatable cuff.

2. The assembly of claim 1, wherein said medical device is an endotracheal tube for use in intubating the patient, said endotracheal tube further comprising a connector at said proximal end of said wall for connecting said endotracheal tube to a ventilating machine, and a mark provided on said wall proximal of said inflatable cuff.

3. The assembly of claim 2, wherein said mark is preferably one inch proximal of said inflatable cuff.

4. The assembly of claim 2, wherein said camera lumen is slidably connected to said endotracheal tube.

5. The assembly of claim 2, wherein said endotracheal tube is a dual branch endotracheal tube.

6. The assembly of claim 1, further including a tongue formed on one of said camera lumen and said wall of said endotracheal tube and a groove formed on the other of said camera lumen and said wall to provide said slidable connection.

7. The assembly of claim 1, further comprising a transmission lumen seated within said passageway and extending from an end thereof, said transmission lumen used for transmitting breath and heartbeat sounds from the patient to a medical professional.

\* \* \* \* \*